US010308656B2

(12) United States Patent
Weterings et al.

(10) Patent No.: US 10,308,656 B2
(45) Date of Patent: Jun. 4, 2019

(54) SMALL MOLECULE INHIBITORS OF KU70/80 AND USES THEREOF

(71) Applicant: ARIZONA BOARD OF REGENTS ON BEHALF OF THE UNIVERSITY OF ARIZONA, Tucson, AZ (US)

(72) Inventors: Eric Weterings, Tucson, AZ (US); Daruka Mahadevan, Tucson, AZ (US); Josef Vagner, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 0 days.

(21) Appl. No.: 15/753,513

(22) PCT Filed: Aug. 16, 2016

(86) PCT No.: PCT/US2016/047173
§ 371 (c)(1),
(2) Date: Feb. 19, 2018

(87) PCT Pub. No.: WO2017/031116
PCT Pub. Date: Feb. 23, 2017

(65) Prior Publication Data
US 2018/0244678 A1 Aug. 30, 2018

Related U.S. Application Data

(60) Provisional application No. 62/206,550, filed on Aug. 18, 2015.

(51) Int. Cl.
*A61K 31/55* (2006.01)
*A61K 45/06* (2006.01)
*A61P 35/00* (2006.01)
*A61K 31/496* (2006.01)
*A61K 31/519* (2006.01)
*C07D 413/12* (2006.01)
*C07D 487/04* (2006.01)

(52) U.S. Cl.
CPC .......... *C07D 487/04* (2013.01); *A61K 31/496* (2013.01); *A61K 31/519* (2013.01); *A61K 31/55* (2013.01); *A61K 45/06* (2013.01); *A61P 35/00* (2018.01); *C07D 413/12* (2013.01)

(58) Field of Classification Search
CPC ..... C07D 487/04; C07D 413/12; A61P 35/00; A61K 31/496; A61K 31/519; A61K 31/55; A61K 45/06
USPC ........................................................ 514/245
See application file for complete search history.

(56) References Cited

U.S. PATENT DOCUMENTS

| 5,733,914 | A | * | 3/1998 | Blankley | .............. | C07D 471/04 514/210.21 |
| 6,150,373 | A | * | 11/2000 | Harris | .................. | C07D 487/04 514/228.5 |
| 6,451,804 | B1 | * | 9/2002 | Dunn | ................... | C07D 487/04 514/262.1 |
| 6,518,276 | B2 | * | 2/2003 | Arzeno | ............... | C07D 239/47 514/264.11 |
| 7,371,750 | B2 | * | 5/2008 | Sim | ...................... | C07D 471/04 514/234.2 |
| 8,436,004 | B2 | * | 5/2013 | Bamba | ................. | A61K 31/522 514/262.1 |
| 8,575,179 | B2 | * | 11/2013 | Bamba | ................. | A61K 31/519 514/262.1 |
| 2009/0118261 | A1 | | 5/2009 | Aquila et al. | | |
| 2014/0314674 | A1 | | 10/2014 | Raymon | | |

FOREIGN PATENT DOCUMENTS

WO   2015/044075   4/2015

OTHER PUBLICATIONS

Chemical Abstracts, STN Registry Database Record for RN 1326852-06-5, 7[[2-(3,4-dimethoxyphenyl)ethyl]amino]-3-(3-fluorophenyl)-pyrimido[4,5-d]pyrimidine-2,4(1H,3H)-dione, Entry Date Sep. 2, 2011. (Year: 2011).*
Chemical Abstracts, STN Registry Database Record for RN 1326827-25-1; 7-(cyclohexylamino)-3-(3-fluorophenyl)-pyrimido[4,5-d]pyrimidine-2,4(1 H,3H)-dione, Entry Date Sep. 2, 2011. (Year: 2011).*
International Search Report and Written Opinion, International Patent Application No. PCT/US2016/047173, dated Oct. 31, 2016, 8 pages.
An, J., M. Totrov, and R. Abagyan. Comprehensive identification of "druggable" protein ligand binding sites. Genome Inform. 2004, 15(2):31-41.
Bao, S., Q. Wu, R.E. McLendon, Y. Hao, Q. Shi, A.B. Hjelmeland, M.W. Dewhirst, D.D. Bigner, and J.N. Rich. 2006. Glioma stem cells promote radioresistance by preferential activation of the DNA damage response. Nature. 444:756-760.
Berger, P.G. Febbo, P.K. Majumder, J.J. Zhao, S. Mukherjee, S. Signoretti, K.T. Campbell, W.R. Sellers, T.M. Roberts, M. Loda, T.R. Golub, W.C. Hahn; Androgen-induced differentiation and tumorigenicity of human prostate epithelial cells; Cancer Res., 64 (2004), pp. 8867-8875.
Beskow, C., J. Skikuniene, A. Holgersson, B. Nilsson, R. Lewensohn, L. Kanter, and K. Viktorsson. 2009. Radioresistant cervical cancer shows upregulation of the NHEJ proteins DNA-PKcs, Ku70 and Ku86. Br J Cancer. 101:816-821.
Curtin N.J. 2012. DNA repair dysregulation from cancer driver to therapeutic target. Nat Rev Cancer. 12:801-817.

(Continued)

Primary Examiner — Daniel R Carcanague
(74) Attorney, Agent, or Firm — Casimir Jones, S.C.; Robert A. Goetz

(57) ABSTRACT

Provided herein are methods for identifying and treating subjects having conditions involving aberrant Ku70/80 activity. In particular, the invention relates to small-molecules which function as inhibitors of Ku70/80 protein and the non-homologous end-joining (NHEJ) pathway, and their use as therapeutics for the treatment of cancer and other diseases.

9 Claims, 9 Drawing Sheets

(56) References Cited

OTHER PUBLICATIONS

Eisenbrey, L. Albala, M.R. Kramer, N. Daroshefski, D. Brown, J.B. Liu, M. Stanczak, P. O'Kane, F. Forsberg, M.A. Wheatley; Development of an ultrasound sensitive oxygen carrier for oxygen delivery to hypoxic tissue; Int. J. Pharm., 478 (2015), pp. 361-367.

Fattah, B.L. Ruis, E.A. Hendrickson; Mutations to Ku reveal differences in human somatic cell lines; DNA Repair (Amst.), 7 (2008), pp. 762-774.

Ghezraoui, H., et al. 2014. Chromosomal translocations in human cells are generated by canonical nonhomologous end-joining. Mol Cell. 55:829-842.

Gu, Y., et al. 1997. Ku70-deficient embryonic stem cells have increased ionizing radiosensitivity, defective DNA end-binding activity, and inability to support V(D)J recombination. Proc Natl Acad Sci U S A. 94:8076-8081.

Han, S., et al. 2013. Targeted radiosensitization of ETS fusion-positive prostate cancer through PARP1 inhibition. Neoplasia. 15:1207-1217.

Irwin, J.J., et al. 2012. ZINC: a free tool to discover chemistry for biology. J Chem Inf Model. 52:1757-1768.

Jaamaa, S., and M. Laiho. 2012. Maintenance of genomic integrity after DNA double strand breaks in the human prostate and seminal vesicle epithelium: the best and the worst. Mol Oncol. 6:473-483.

Jekimovs, C., et al. 2014. Chemotherapeutic compounds targeting the DNA double-strand break repair pathways: the good, the bad, and the promising. Front Oncol. 4:86.

Jubb, H., et al. 2012. Structural biology and drug discovery for protein-protein interactions. Trends Pharmacol Sci. 33:241-248.

Kim, S.H., et al. 1999. Ku autoantigen affects the susceptibility to anticancer drugs. Cancer Res. 59:4012-4017.

Klibanov, T.I. et al.; Ultrasound-triggered release of materials entrapped in microbubble-liposome constructs: a tool for targeted drug delivery; J. Control. Release, 148 (2010), pp. 13-17.

Kragelund, E et al.; The Ku70/80 ring in Non-homologous End-joining: easy to slip on hard to remove; Front Biosci. (Landmark Ed), 21 (2016), pp. 514-527.

Li, Y.H., et al.2012. Inhibition of non-homologous end joining repair impairs pancreatic cancer growth and enhances radiation response. PLoS One. 7:e39588.

Moding, E.J., M.B. Kastan, and D.G. Kirsch. 2013. Strategies for optimizing the response of cancer and normal tissues to radiation. Nat Rev Drug Discov. 12:526-542.

Nimura, Y., et al. 2007. Silencing Ku80 using small interfering RNA enhanced radiation sensitivity in vitro and in vivo. Int J Oncol. 30:1477-1484.

Perot, S., et al. 2010. Druggable pockets and binding site centric chemical space: a paradigm shift in drug discovery Drug Discov Today. 15:656-667.

Smith, G.C., and S.P. Jackson. 1999. The DNA-dependent protein kinase. Genes Dev. 13:916-934.

Walker, J.R., R.A. Corpina, and J. Goldberg. 2001. Structure of the Ku heterodimer bound to DNA and its implications for double-strand break repair. Nature. 412:607-614.

Welsh, J.W., et al. 2009. The c-Met receptor tyrosine kinase inhibitor MP470 radiosensitizes glioblastoma cells. Radiat Oncol. 4:69.

Weterings, E., and D.J. Chen. 2008. The endless tale of non-homologous end-joining. Cell Res. 18:114-124.

Weterings, E., et al. 2003. The role of DNA dependent protein kinase in synapsis of DNA ends. Nucleic Acids Res. 31:7238-7246.

\* cited by examiner

FIG. 2
A
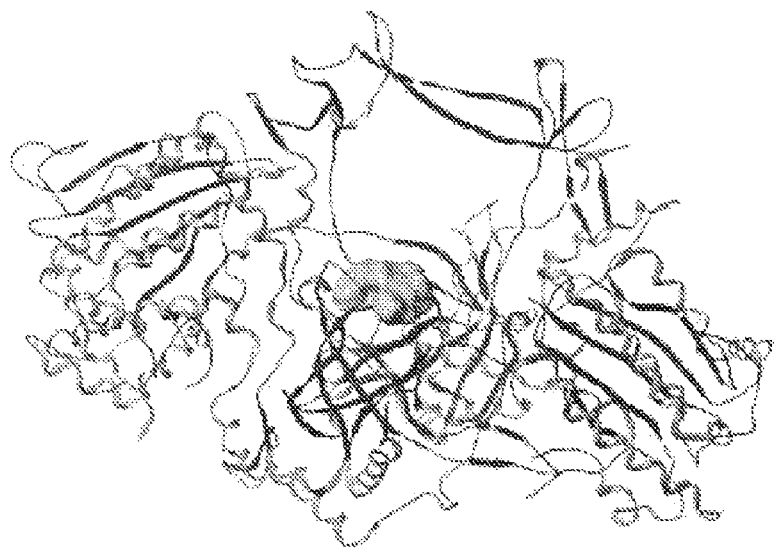
B
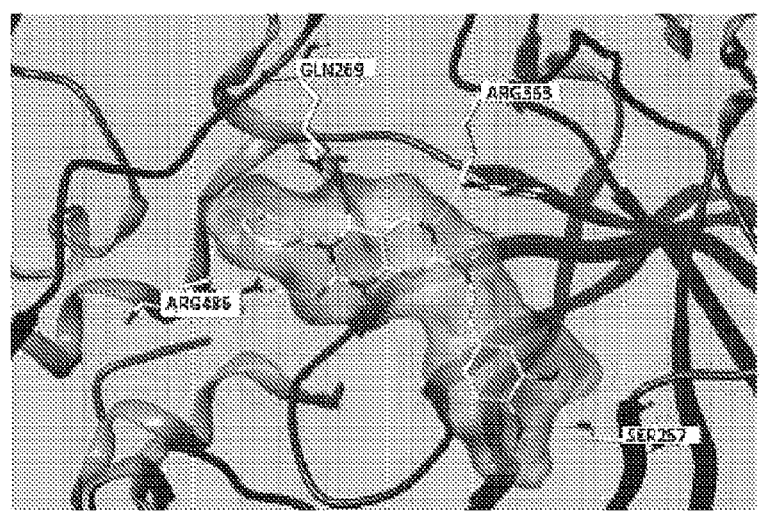
C
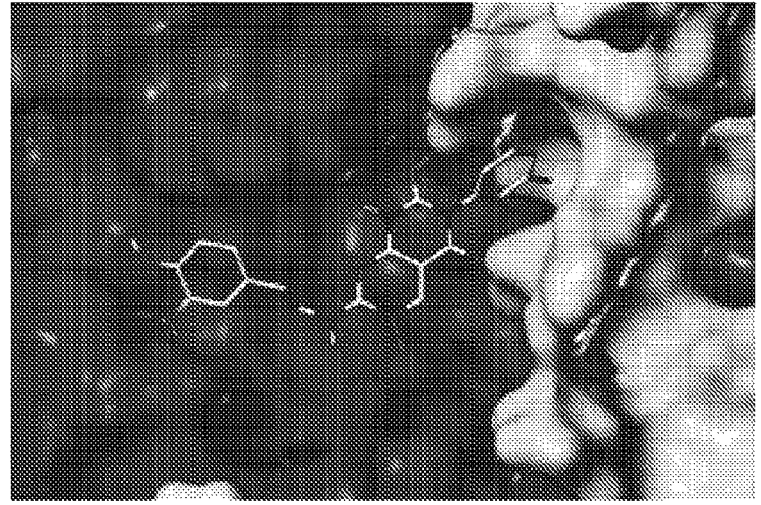

FIG. 3
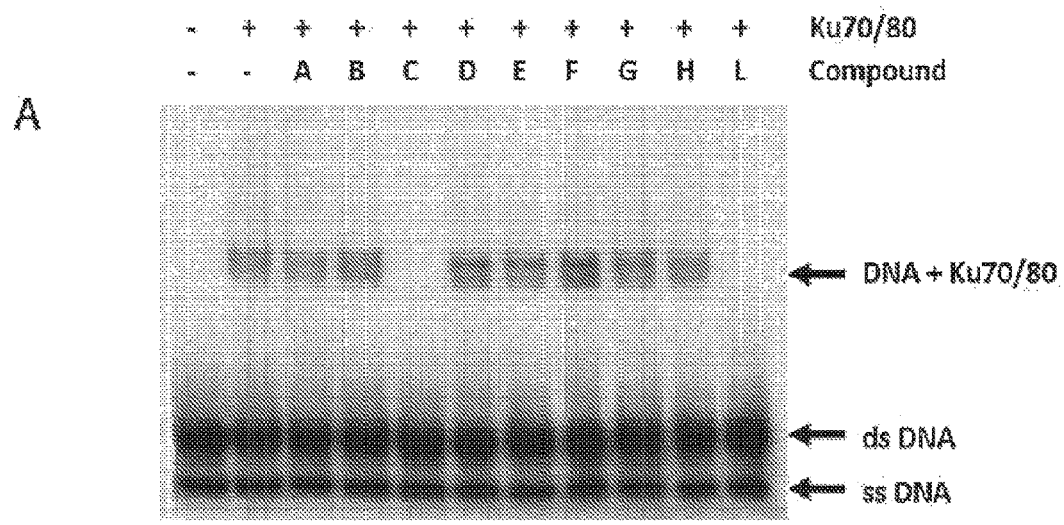
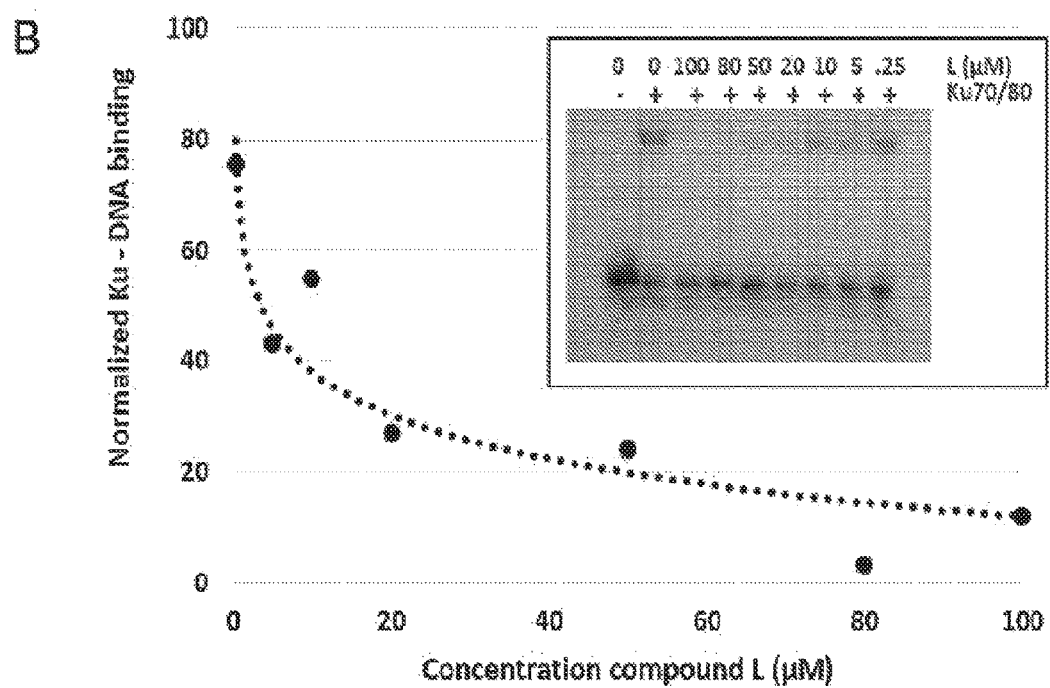

| PK Parameter | 1 mg/kg | 3 mg/kg | 5 mg/kg |
|---|---|---|---|
| half-life (hr) | 1.28 | 1.20 | 1.96 |
| Tmax (hr) | 1 | 1 | 1 |
| Cmax ± SE (ng/mL) | 185.2 ± 33.9 | 432.1 ± 212.2 | 1359.0 ± 565.0 |
| Cmax/Dose (kg*ng/mL/mg) | 185.1 | 144.0 | 271.8 |

SMALL MOLECULE INHIBITORS OF KU70/80 AND USES THEREOF

CROSS-REFERENCE TO RELATED APPLICATIONS

This application is a U.S. 371 national phase entry of International Patent Application No. PCT/US2016/047173, filed Aug. 16, 2016, which claims priority to and the benefit of U.S. Provisional Application No. 62/206,550, filed Aug. 18, 2015, which are hereby incorporated by reference in their entireties.

STATEMENT REGARDING FEDERALLY SPONSORED RESEARCH OR DEVELOPMENT

This invention was made with government support under Grant No. P30 CA023074 awarded by NIH. The government has certain rights in the invention.

FIELD OF THE INVENTION

This invention is in the field of medicinal chemistry. Provided herein are compositions and methods for treating subjects having conditions involving Ku70/80 activity. In particular, the invention relates to small-molecules which function as inhibitors of Ku70/80 protein and the non-homologous end-joining (NHEJ) pathway, and their use as therapeutics for the treatment of cancer and other diseases.

INTRODUCTION

Repair of DNA double-strand breaks (DSBs) is crucial for normal cells to maintain genomic integrity and abnormalities in DSB repair pathways are often observed in tumor cells, resulting in high levels of DNA synthetic errors, translocations and genetic mutations (see, e.g., Sato, et al., (1991). Cancer Res. 51, 5794-5799; Sekowsky, et al., (1998) Cancer Res. 58, 3259-3263). Overexpression or upregulation of DSB repair pathways can result in accumulation of incorrectly repaired DNA lesions and a marked insensitivity to anti-cancer therapies which are based on the introduction of DSBs, such as certain types of chemotherapy or radiation therapy (see, e.g., Kessell (1994) In Vivo 8, 829-834; Morgan, et al., (1995) Cancer Metastasis Rev. 14, 49-58; Powell and Abraham (1993) Cytotechnology 12, 325-345; Kinsella, et al., (1997) Br. J. Cancer 75, 935-945). In such cases, suppression of DSB repair capacity has the potential to re-sensitize tumor cells to chemo- or radiation therapy. In addition, certain tumor types may become dependent on overexpression or upregulation of DSB repair pathways for hyper proliferation. In such cases, suppression of DSB repair capacity—e.g. by means of synthetic lethality—has the potential to impair hyper proliferation.

The present invention relates to small molecule inhibitors of the Ku70/80 heterodimer protein, an important regulator of the NHEJ-mediated DSB repair pathway and their application towards the treatment of cancer and other diseases, either as a single modality therapy, or in combination with chemotherapeutics or radiation therapy.

Improved methods for correcting alterations in DNA repair machinery within cancer cells are needed.

SUMMARY OF THE INVENTION

Non-Homologous End-Joining (NHEJ) is the predominant pathway for the repair of DNA double strand breaks (DSBs) in human cells. The NHEJ pathway is frequently upregulated in several solid cancers as a compensatory mechanism for a separate DSB repair defect or for innate genomic instability, making this pathway a powerful target for synthetic lethality approaches. In addition, NHEJ reduces the efficacy of cancer treatment modalities which rely on the introduction of DSBs, like radiation therapy or genotoxic chemotherapy. Consequently, inhibition of the NHEJ pathway can modulate a radiation- or chemo-refractory disease presentation. The Ku70/80 heterodimer protein plays a pivotal role in the NHEJ process. It possesses a ring-shaped structure with high affinity for DSBs and serves as the first responder and central scaffold around which the rest of the repair complex is built. Because of this central position, the Ku70/80 dimer is a logical target for the disruption of the entire NHEJ pathway. Surprisingly, specific inhibitors of the Ku70/80 heterodimer are currently not available.

Experiments conducted during the course of developing embodiments for the present invention discovered a novel prospective ligand binding pocket in the Ku70/80 crystal structure. In addition, such experiments conducted computational and biological screening of potential small molecule inhibitors of Ku70/80. Such experiments resulted in the first identification of two compounds

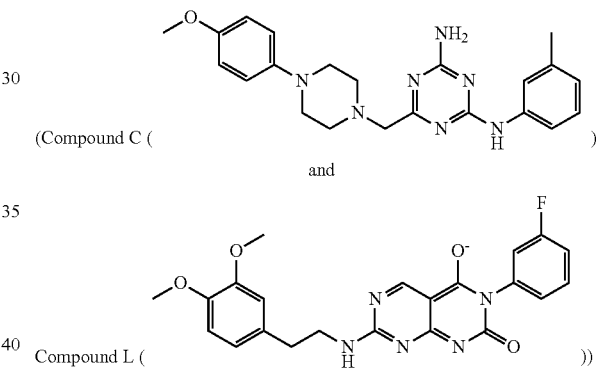

(Compound C ( ) and Compound L ( ))

with confirmed Ku-inhibitory activity in the low micromolar range, capable of disrupting the binding of Ku70/80 to DNA substrates and impairing Ku-dependent activation of another NHEJ factor, DNA-PK$_{CS}$. Importantly, both compounds synergistically sensitized human glioblastoma cells to radiation treatment at sub-cytotoxic concentrations, indicating a clear potential to diminish DSB repair.

Additional experiments conducted during the course of developing embodiments for the present invention further identified the following compounds capable of disrupting the binding of Ku70/80 to DNA substrates and/or impairing Ku-dependent activation of DNA-PK$_{CS}$:

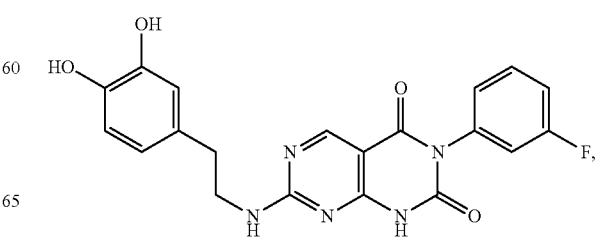

(761)

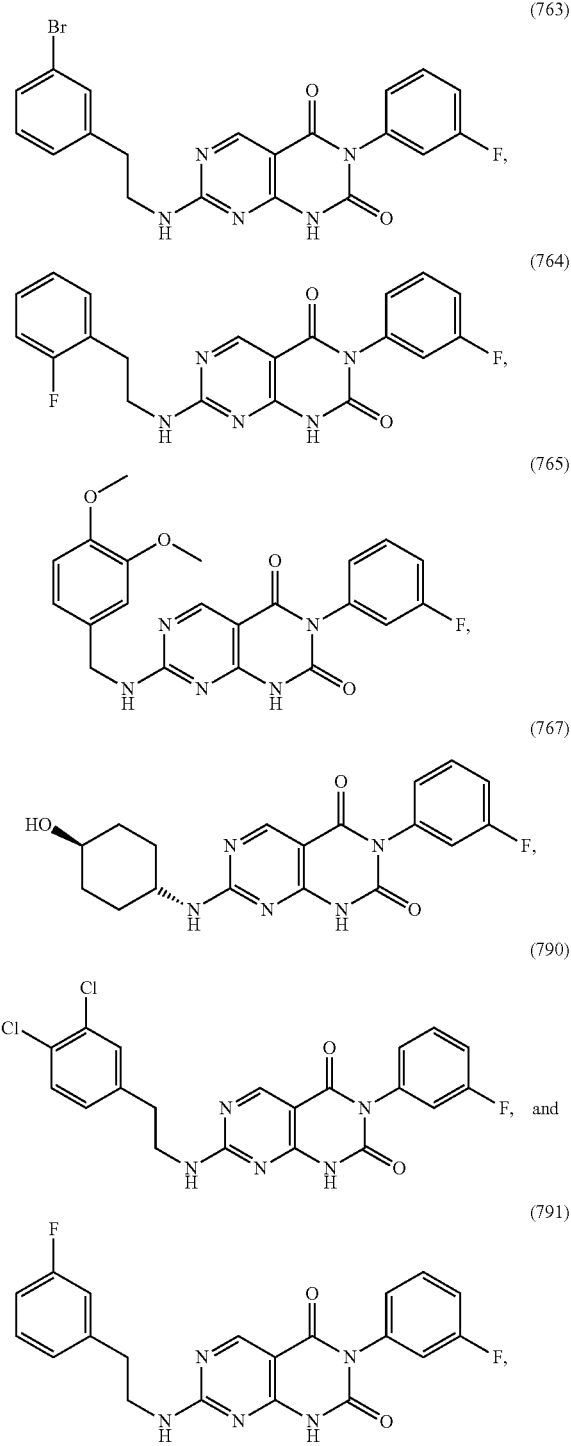

Accordingly, provided herein are compositions and methods for treating subjects having conditions involving an aberrant, overexpressed or upregulated Ku70/80 profile, or subjects having conditions which can be ameliorated by diminishing Ku70/80-mediated DSB repair. In particular, the invention relates to small-molecules which function as inhibitors of the Ku70/80 protein and the non-homologous end-joining (NHEJ) pathway, and their use as therapeutics for the treatment of cancer and other diseases.

The present invention contemplates that certain cancers and/or cancer-related disorders in animals (e.g. humans) can be treated, ameliorated, or prevented by exposure to therapeutically effective amounts of drug(s) capable of inhibiting Ku70/80 activity, and/or drug(s) capable of preventing engagement of Ku70/80 with DNA, and/or drug(s) capable of rendering cancer cells as a population more susceptible to the cell death-inducing activity of cancer therapeutic drugs or radiation therapies, and/or drugs capable of inhibiting the NHEJ pathway related activity (e.g., any of the compounds of the present invention identified as capable of disrupting the binding of Ku70/80 to DNA substrates and/or impairing Ku-dependent activation of DNA-PK$_{CS}$) (e.g., compounds having a structure similar to Compound C) (e.g., compounds having a structure similar to Compound L).

In some embodiments, the inhibition of Ku70/80 activity occurs through, for example, inhibiting the interaction between Ku70/80 and a DNA substrate. In some embodiments, the inhibition of Ku70/80 activity occurs through, for example, binding a ligand binding pocket in Ku70/80 (described in the Examples). The present invention contemplates that inhibitors of Ku70/80 activity satisfy an unmet need for the treatment of multiple cancer types involving aberrant Ku70/80 activity and/or NHEJ pathway related activity, either when administered as monotherapy to induce cell growth inhibition, cell death and/or cell cycle arrest in cancer cells, or when administered in a temporal relationship with additional agent(s), such as other cell death-inducing or cell cycle disrupting cancer therapeutic drugs or radiation therapies (combination therapies), so as to render a greater proportion of the cancer cells or supportive cells susceptible to executing the cell death program compared to the corresponding proportion of cells in a subject treated only with the cancer therapeutic drug or radiation therapy alone.

In certain embodiments of the invention, combination treatment of subjects with a therapeutically effective amount of a compound of the present invention and a course of an anticancer agent produces a greater tumor response and clinical benefit in such subjects compared to those treated with the compound or anticancer drugs/radiation alone. Since the doses for all approved anticancer drugs and radiation treatments are known, the present invention contemplates the various combinations of them with the present compounds.

The Applicants have found that certain compounds are capable of disrupting the binding of Ku70/80 to DNA substrates and/or impairing Ku-dependent activation of DNA-PK$_{CS}$, and as such, serve as therapeutics for the treatment of cancer and other diseases. Thus, the present invention relates to compounds capable of disrupting the binding of Ku70/80 to DNA substrates and/or impairing Ku-dependent activation of DNA-PK$_{CS}$, and increasing the sensitivity of cells to inducers of apoptosis and/or cell cycle arrest.

In certain embodiments, the following compounds are provided as capable of disrupting the binding of Ku70/80 to DNA substrates, and/or capable of inhibiting Ku70/80 activity, and/or capable of rendering cancer cells as a population more susceptible to the cell death-inducing activity of cancer therapeutic drugs or radiation therapies, and/or capable of inhibiting the NHEJ pathway related activity, and/or impairing Ku-dependent activation of DNA-PK$_{CS}$, and as such, serve as therapeutics for the treatment of cancer and other diseases:

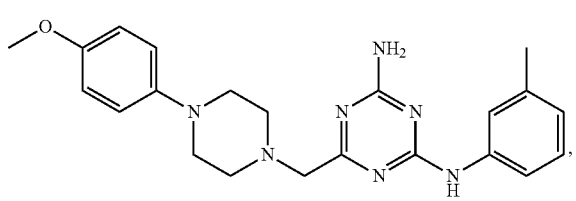
(Compound C and structures similar to Compound C)
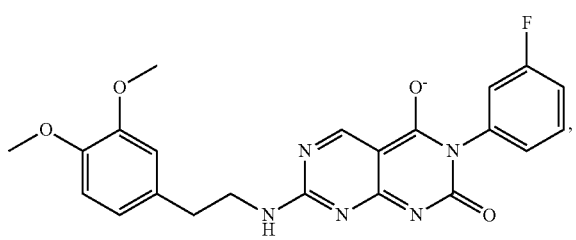
(Compound L and structures similar to Compound L)
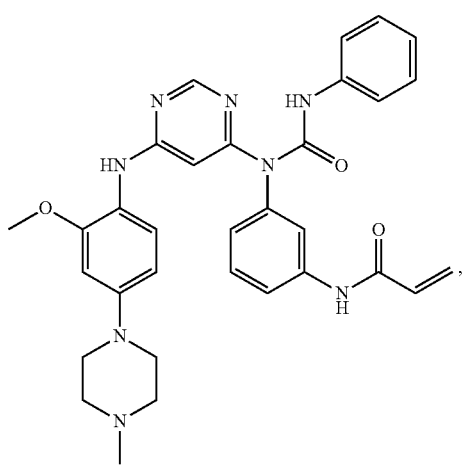
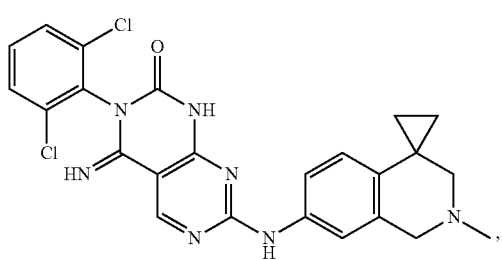
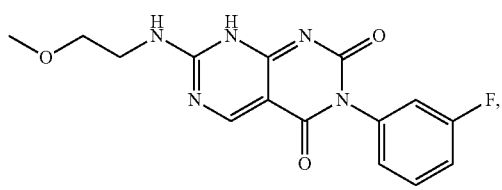
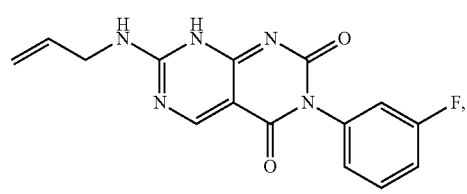
-continued
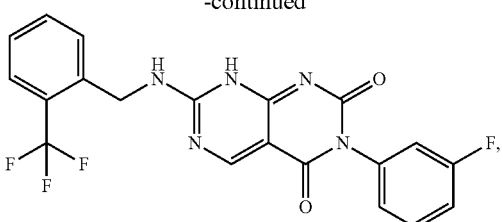
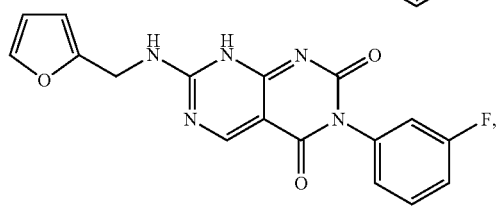
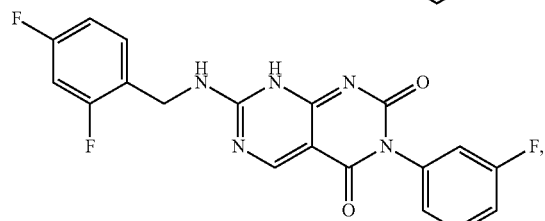
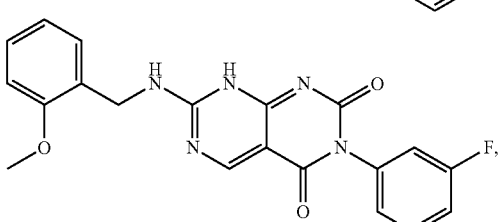
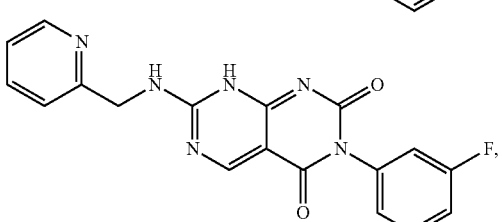
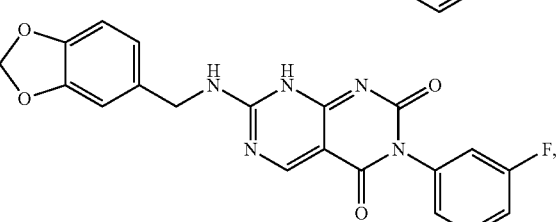
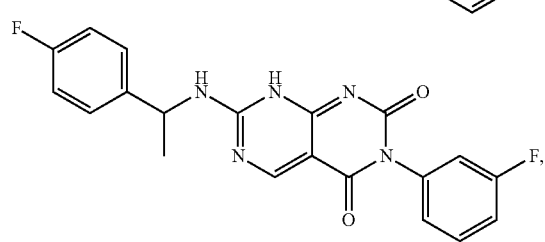
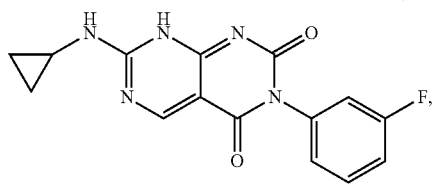

-continued
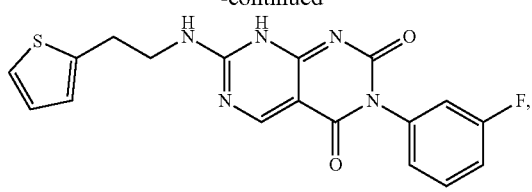
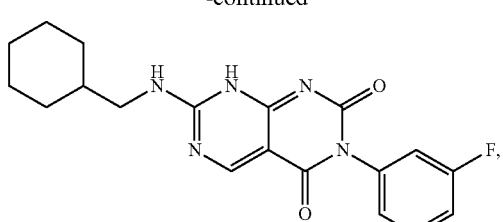
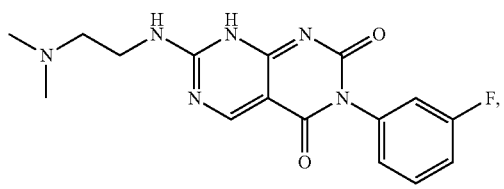
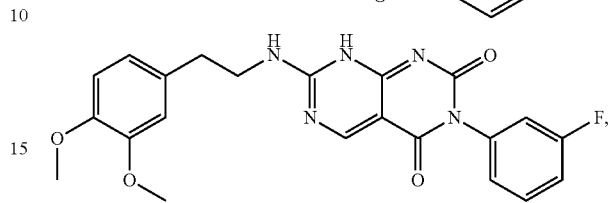
(760)
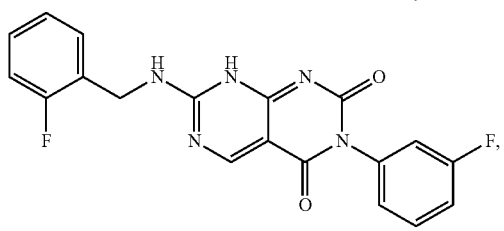
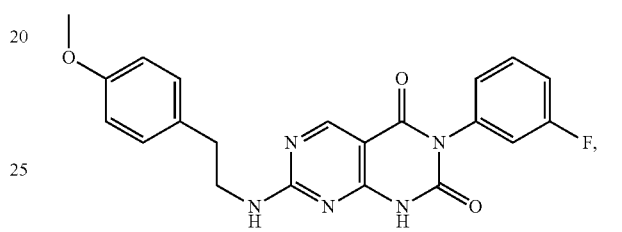
(761)
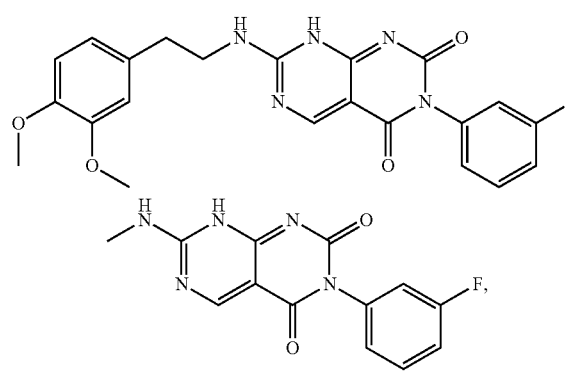
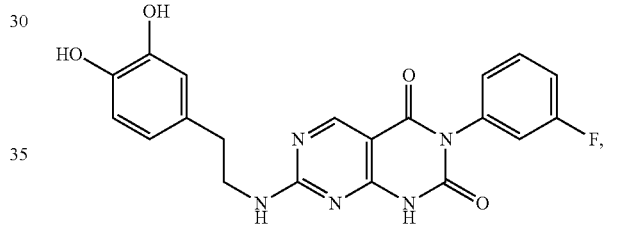
(762)
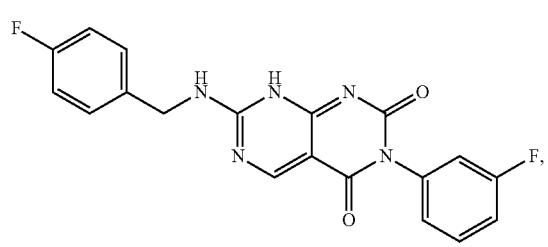
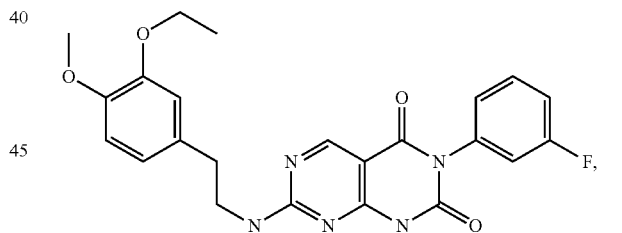
(763)
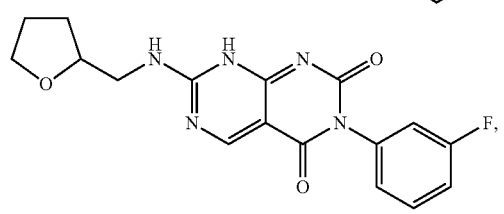
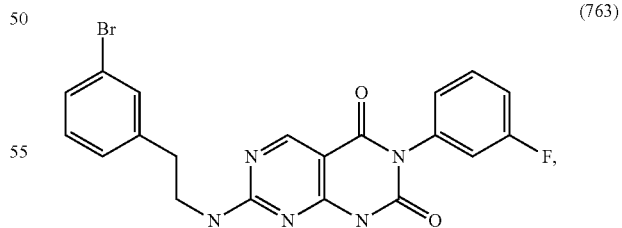
(764)
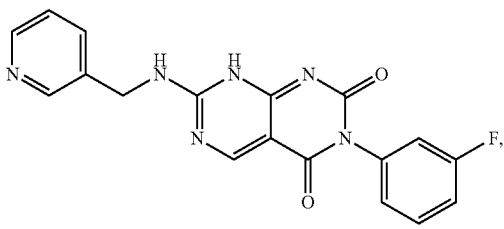
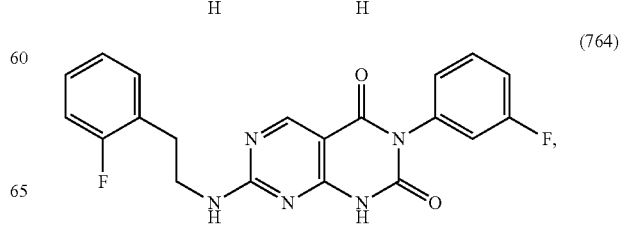

-continued (765)

(766)

(767)

(788)

(789)

(790)

(791)

-continued

-continued

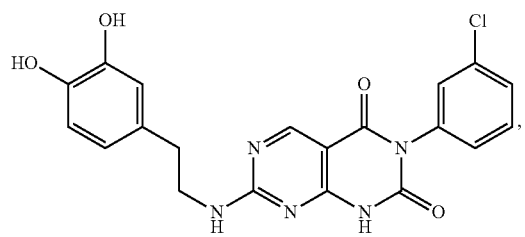

or a pharmaceutically acceptable salt, solvate, or prodrug thereof.

Such compounds of the present invention may exist as stereoisomers including optical isomers. Indeed, the invention includes all stereoisomers, both as pure individual stereoisomer preparations and enriched preparations of each, and both the racemic mixtures of such stereoisomers as well as the individual diastereomers and enantiomers that may be separated according to methods that are well known to those of skill in the art. The invention further provides processes for preparing any of the compounds of the present invention.

In certain embodiments, the compounds of the invention are useful for the treatment, amelioration, or prevention of any disorder that is responsive to the induction of DSBs and the cellular effects thereof (e.g., disorders characterized by dysregulation of DNA repair, cell cycle arrest mechanisms, and cell death mechanisms, including hyperproliferative diseases such as cancer). In certain embodiments, the compounds can be used to treat, ameliorate, or prevent cancer that is characterized by resistance to cancer therapies (e.g., those cancer cells which are chemoresistant, radiation resistant, hormone resistant, and the like). In certain embodiments, the cancer is glioblastoma. In other embodiments, the compounds can be used to treat hyperproliferative diseases characterized by aberrant expression of Ku70/80 proteins.

The invention also provides the use of such compounds to induce inhibition of cell growth, cell cycle arrest and/or cell death in cells with an aberrant Ku70/80 profile. The invention also relates to the use of such compounds for sensitizing cells to additional agent(s), such as inducers of DSBs, cell death and/or cell cycle arrest, and chemoprotection of normal cells through the induction of cell cycle arrest prior to treatment with chemotherapeutic agents.

The invention also provides pharmaceutical compositions comprising the compounds of the invention in a pharmaceutically acceptable carrier.

In certain embodiments, the present invention provides one or more of the following compounds:

(761)

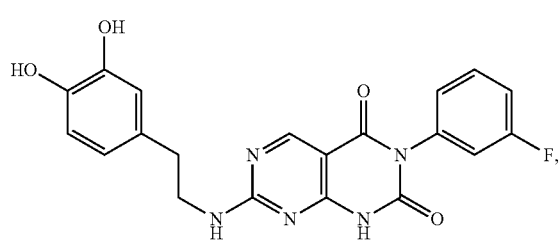

-continued (762)

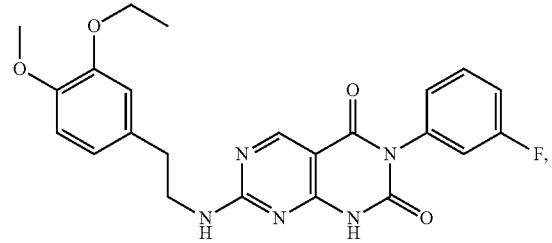

(763)

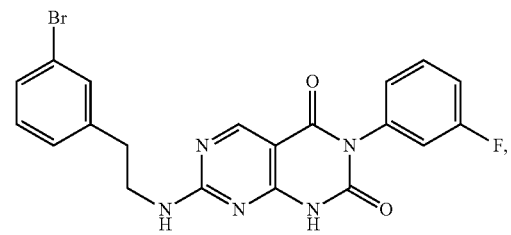

(764)

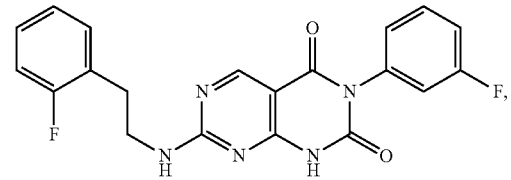

(767)

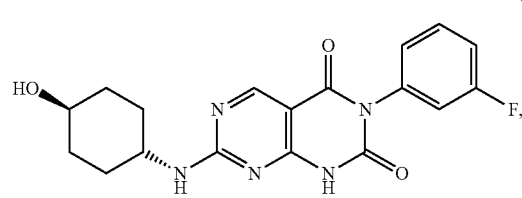

(788)

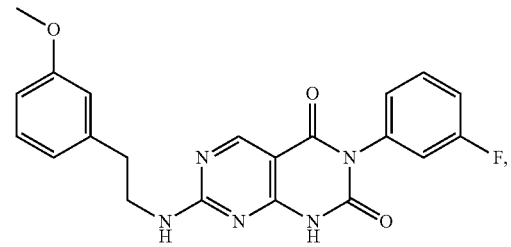

(789)

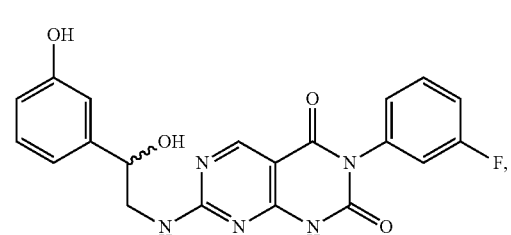

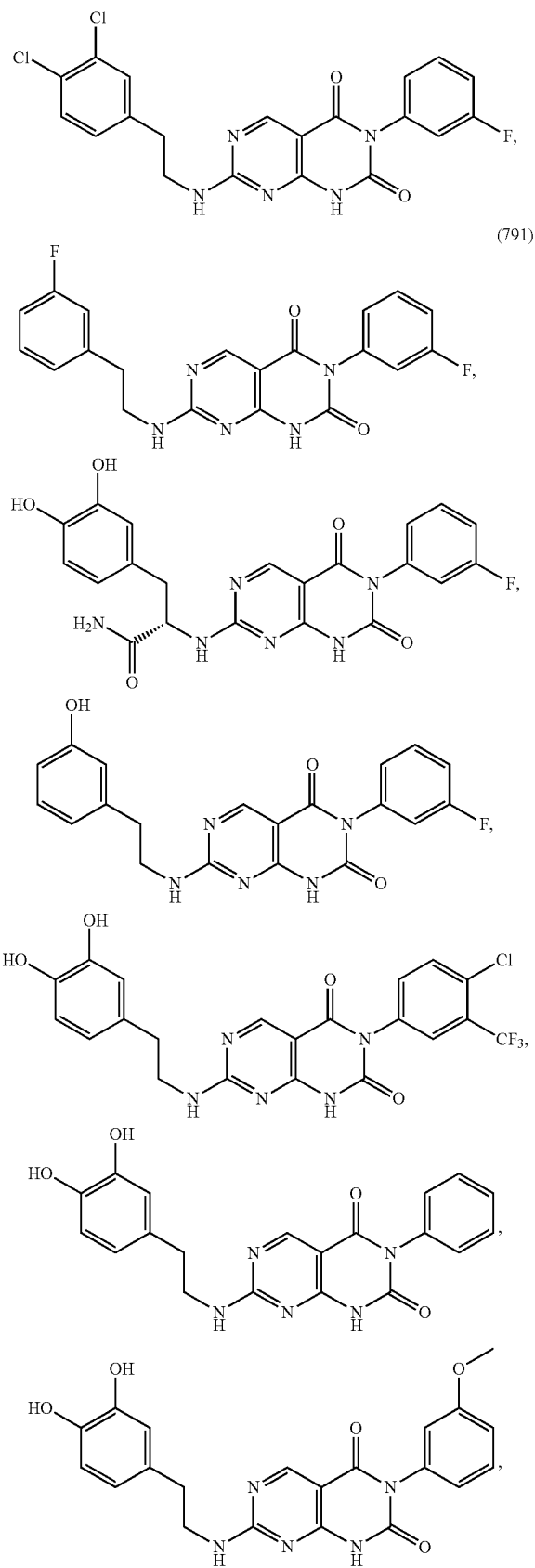

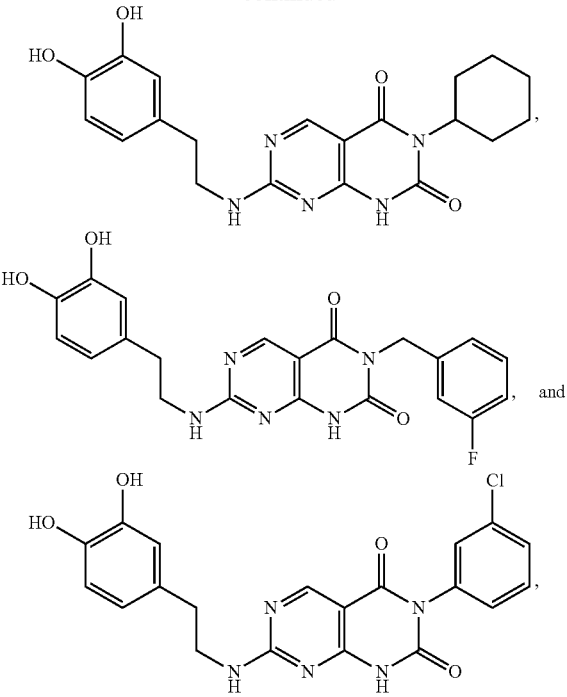

including pharmaceutically acceptable salts, solvates, and/or prodrugs thereof.

In some embodiments, the compound is comprised within a pharmaceutical composition.

The invention also provides kits comprising a compound of the invention and instructions for administering the compound to an animal. The kits may optionally contain other therapeutic agents, e.g., anticancer agents or apoptosis-modulating agents.

BRIEF DESCRIPTION OF DRAWINGS

FIG. 2A-C. Identification of a putative drug binding pocket in the Ku70/80 crystal structure and interactive docking of Compound L. (A) Ku70/80 crystal structure (PDB ID: 1JEQ) with location of the putative binding pocket (turquoise) close to the central DNA-binding canal and the Ku70-Ku80 heterodimer interface. (B) Depiction of Compound L docked in the putative drug binding pocket with predicted hydrogen bonds between amino acid residues and Compound L indicated. (C) Depiction of Compound L docked in the putative drug binding pocket. Red surface indicates Ku70's contribution to the pocket and yellow surface indicates Ku80's contribution.

FIG. 3A-B. Compound L inhibits binding of Ku70/80 to a DNA substrate. (A) Biological activity screening of 9 selected candidate compounds by means of an Electrophoretic Mobility Shift Assay (EMSA). Compounds C and L screen positive for disruption of Ku70/80-DNA interaction at 100 μM, as indicated by the absence of a Ku-DNA band. (B) Titration of Compound L in the EMSA assay. A logarithmic trend line (dotted line) is added. An $IC_{50}$ of 3.5 µM can be calculated from this graph.

As shown in FIG. 8 at the 25 µM location, JV761 has the lowest DNA-$PK_{CS}$ kinase activity, followed by JV765, followed by JV767, and followed by JV763.

DEFINITIONS

Figure 1:
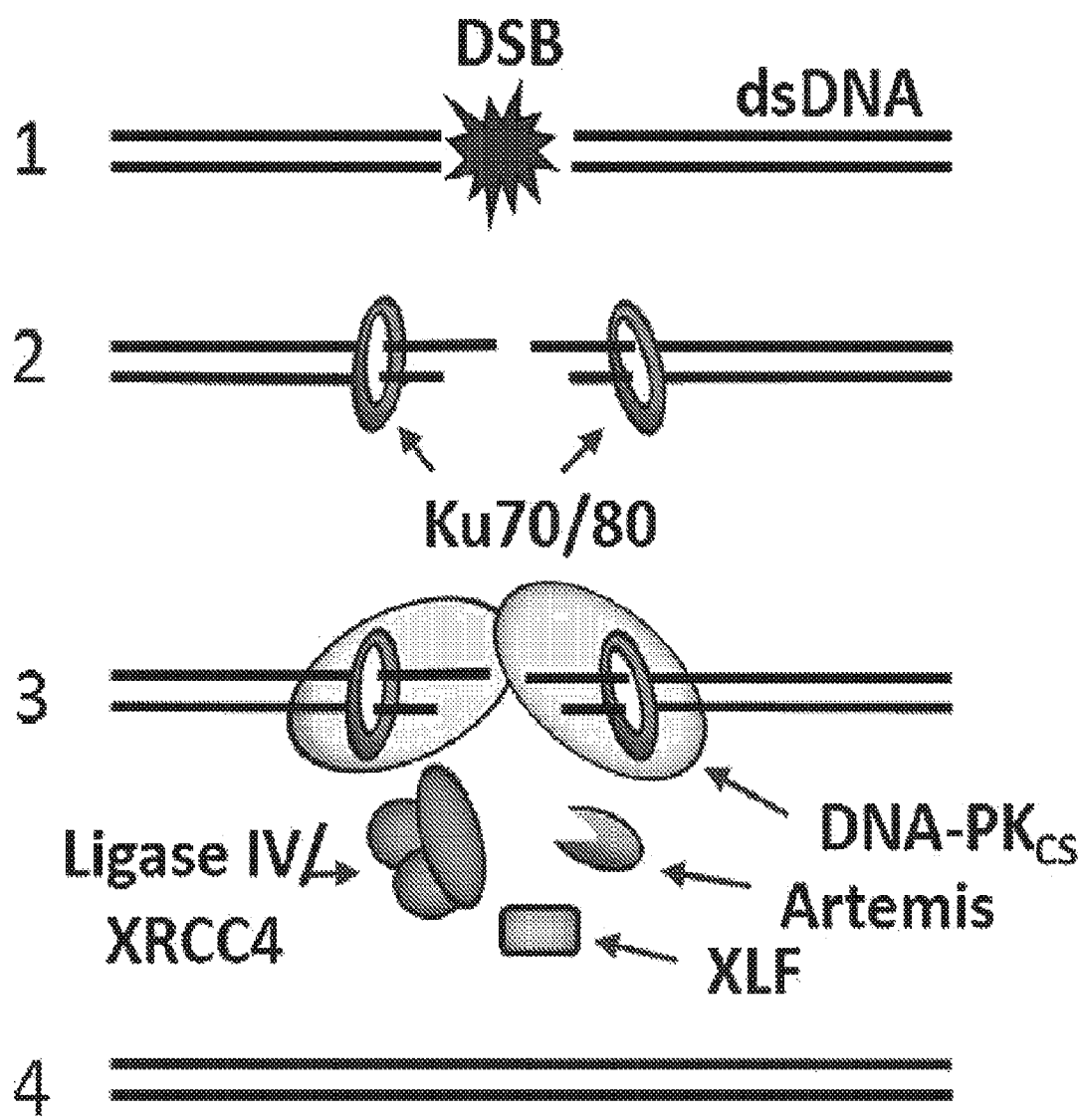
FIG. 1. Schematic overview of NHEJ and the central role of Ku70/80. 1) a DSB is introduced; 2) the ring-shaped Ku70/80 heterodimer protein associates with the DNA termini; 3) Ku70/80 attracts and activates additional NHEJ factors, including DNA-PK$_{CS}$, and a bridge is formed between the two DNA ends, ultimately resulting in 4) repair of the DSB.

The term "anticancer agent" as used herein, refer to any therapeutic agents (e.g., chemotherapeutic compounds and/or molecular therapeutic compounds), antisense therapies, radiation therapies, or surgical interventions, used in the treatment of hyperproliferative diseases such as cancer (e.g., in mammals, e.g., in humans).

The term "prodrug" as used herein, refers to a pharmacologically inactive derivative of a parent "drug" molecule that requires biotransformation (e.g., either spontaneous or enzymatic) within the target physiological system to release, or to convert (e.g., enzymatically, physiologically, mechanically, electromagnetically) the prodrug into the active drug. Prodrugs are designed to overcome problems associated with stability, water solubility, toxicity, lack of specificity, or limited bioavailability. Exemplary prodrugs comprise an active drug molecule itself and a chemical masking group (e.g., a group that reversibly suppresses the activity of the drug). Some prodrugs are variations or derivatives of compounds that have groups cleavable under metabolic conditions. Prodrugs can be readily prepared from the parent compounds using methods known in the art, such as those described in A Textbook of Drug Design and Development, Krogsgaard-Larsen and H. Bundgaard (eds.), Gordon & Breach, 1991, particularly Chapter 5: "Design and Applications of Prodrugs"; Design of Prodrugs, H. Bundgaard (ed.), Elsevier, 1985; Prodrugs: Topical and Ocular Drug Delivery, K. B. Sloan (ed.), Marcel Dekker, 1998; Methods in Enzymology, K. Widder et al. (eds.), Vol. 42, Academic Press, 1985, particularly pp. 309-396; Burger's Medicinal Chemistry and Drug Discovery, 5th Ed., M. Wolff (ed.), John Wiley & Sons, 1995, particularly Vol. 1 and pp. 172-178 and pp. 949-982; Pro-Drugs as Novel Delivery Systems, T. Higuchi and V. Stella (eds.), Am. Chem. Soc., 1975; and Bioreversible Carriers in Drug Design, E. B. Roche (ed.), Elsevier, 1987.

Exemplary prodrugs become pharmaceutically active in vivo or in vitro when they undergo solvolysis under physiological conditions or undergo enzymatic degradation or other biochemical transformation (e.g., phosphorylation, hydrogenation, dehydrogenation, glycosylation). Prodrugs often offer advantages of water solubility, tissue compatibility, or delayed release in the mammalian organism. (See e.g., Bundgard, Design of Prodrugs, pp. 7-9, 21-24, Elsevier, Amsterdam (1985); and Silverman, The Organic Chemistry of Drug Design and Drug Action, pp. 352-401, Academic Press, San Diego, Calif. (1992)). Common prodrugs include acid derivatives such as esters prepared by reaction of parent acids with a suitable alcohol (e.g., a lower alkanol) or esters prepared by reaction of parent alcohol with a suitable carboxylic acid, (e.g., an amino acid), amides prepared by reaction of the parent acid compound with an amine, basic groups reacted to form an acylated base derivative (e.g., a lower alkylamide), or phosphorus-containing derivatives, e.g., phosphate, phosphonate, and phosphoramidate esters, including cyclic phosphate, phosphonate, and phosphoramidate (see, e.g., US Patent Application Publication No. US 2007/0249564 A1).

The term "pharmaceutically acceptable salt" as used herein, refers to any salt (e.g., obtained by reaction with an acid or a base) of a compound of the present invention that is physiologically tolerated in the target animal (e.g., a mammal). Salts of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, mesylate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

The term "solvate" as used herein, refers to the physical association of a compound of the invention with one or more solvent molecules, whether organic or inorganic. This physical association often includes hydrogen bonding. In certain instances, the solvate is capable of isolation, for example, when one or more solvate molecules are incorporated in the crystal lattice of the crystalline solid. "Solvate" encompasses both solution-phase and isolable solvates. Exemplary solvates include hydrates, ethanolates, and methanolates.

The term "therapeutically effective amount," as used herein, refers to that amount of the therapeutic agent sufficient to result in amelioration of one or more symptoms of a disorder, or prevent advancement of a disorder, or cause regression of the disorder. For example, with respect to the treatment of cancer, in one embodiment, a therapeutically effective amount will refer to the amount of a therapeutic agent that decreases the rate of tumor growth, decreases tumor mass, decreases the number of metastases, increases time to tumor progression, or increases survival time by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

The terms "sensitize" and "sensitizing," as used herein, refer to making, through the administration of a first agent to an animal or a cell within an animal for purposes of rendering the cell more susceptible, or more responsive, to the biological effects (e.g., promotion or retardation of an aspect of cellular function including, but not limited to, cell division, cell growth, proliferation, invasion, angiogenesis, necrosis, or apoptosis) of a second agent. The sensitizing effect of a first agent on a target cell can be measured as the difference in the intended biological effect (e.g., promotion or retardation of an aspect of cellular function including, but not limited to, cell growth, proliferation, invasion, angiogenesis, or apoptosis) observed upon the administration of a second agent with and without administration of the first agent. The response of the sensitized cell can be increased by at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 450%, or at least about 500% over the response in the absence of the first agent.

DETAILED DESCRIPTION OF THE INVENTION

The Ku 70/80 heterodimer protein serves as the central regulating factor during repair of DNA double-strand breaks (DSBs) via the Non-Homologous End-Joining (NHEJ) pathway. The NHEJ process is a highly conserved pathway which developed at an early stage in evolution to counteract the deleterious effects of background radiation and genotoxic substances. Although critical to the survival of healthy tissue, the NHEJ pathway can also be involved in carcinogenesis or reduce the efficacy of anti-cancer treatments which are based on the introduction of DSBs, like radiation therapy (RT) and genotoxic chemotherapy (Curtin, 2012; Moding et al., 2013). For this reason, the NHEJ process is a logical target for therapies based on either synthetic lethality or on sensitization of tumors to RT or chemotherapy or targeted therapies including immune checkpoint modulators.

Many solid tumors display upregulated expression or activation of NHEJ repair factors, presumably as a compensatory mechanism for the increased genomic instability caused by a separate mutator-type DNA repair defect (Curtin, 2012). For instance, a deficiency in the secondary DSB repair pathway, Homologous Recombination, would render a tumor entirely dependent on NHEJ. This enhanced NHEJ capability, in turn, can drive further oncogenic events such as gene fusions in prostate, bone, and breast cancers (Ghezraoui et al., 2014; Han et al., 2013; Jaamaa and Laiho, 2012). Several key NHEJ factors (including Ku70/80) were found to be unregulated in cervical as well as pancreatic cancers and contributed to both radiation-resistance and overall proliferation of these solid cancers (Beskow et al., 2009; Jekimovs et al., 2014; Li et al., 2012). Disruption of NHEJ in vitro resulted in impaired tumor growth and increased radiation-sensitivity, clearly demonstrating that the tumor's dependency on a Ku70/80- or NHEJ-mediated compensatory mechanism is also a weakness which can be exploited in a synthetic lethality approach to treatment (Li et al., 2012).

The NHEJ pathway is not only implicated in driving oncogenic events, but it is also the single most effective process responsible for reducing the efficacy of DSB-inducing therapies for solid cancers. NHEJ is active during all stages of the cell cycle and is accountable for the rapid repair of an estimated 85% of radiation-induced lesions (Jekimovs et al., 2014). These considerations make the NHEJ pathway a potent and well-recognized target for the development of RT- or chemo-sensitizing compounds (Jekimovs et al., 2014). Obviously, such drugs would be most effective and naturally selective for NHEJ-dependent tumors. However, they could also serve to sensitize tumors with an unaltered NHEJ background, provided that a mechanism for selective targeting of the drug to cancerous tissue is available.

Initiation of the NHEJ pathway is highly dependent on the Ku70/80 heterodimer, making this protein the most logical choice for inhibition of the entire NHEJ process. Upon the introduction of a DSB, NHEJ-mediated repair commences by association of the Ku70/80 heterodimer with both ends of the broken DNA molecule (FIG. 1A). The crystal structure of the Ku70/80 dimer reveals a ring-shaped structure with a central canal which closely accommodates a DNA helix (Walker et al., 2001). As a result, the Ku70/80 ring essentially slides over the DNA termini, independent of nucleotide sequence patterns. This unique feature explains the high affinity of Ku70/80 for DNA ends and the Ku-DNA association is currently thought to be the primary scaffold which attracts and activates all other NHEJ core proteins, including the DNA-Dependent Protein Kinase Catalytic Subunit (DNA-PK$_{CS}$), the XRCC4-ligase IV complex, XRCC4-Like Factor (XLF), and several processing enzymes (FIG. 1A). Collectively, these factors bring the two termini of the severed DNA molecule together in a synaptic complex and execute subsequent processing and the ultimate restoration of the DSB by direct re-ligation of the DNA termini (Weterings and Chen, 2008).

Disabling the binding of the Ku70/80 heterodimer to the DNA termini incapacitates the entire NHEJ process. This is adequately demonstrated by the well-established fact that Ku70 or Ku80 deficiency leads to profound sensitization to both radiation and radiomimetic chemotherapeutics (Gu et al., 1997; Kim et al., 1999; Nimura et al., 2007). Although the idea of developing inhibitors which target the Ku70/80-DNA interaction is not novel, no such specific inhibitors have been published in the peer-reviewed literature to date (Jekimovs et al., 2014). In part, this may be due to the relatively smooth surface of the central canal of the Ku70/80 ring, which is sparse in yielding suitable binding pockets for small molecules (Walker et al., 2001).

Experiments conducted during the course of developing embodiments for the present invention involve the identification of a prospective binding pocket in the Ku70/80 heterodimer structure, located in a central region which is predicted to mediate interaction between the two subunits of the protein, Ku 70 and Ku80, as well as interaction between Ku70/80 and DNA. Computational (virtual) screening of small molecule libraries allowed selection of nine compounds with a predicted fit to the prospective pocket. These compounds were subsequently tested for biological activity and two compounds (designated as Compound C and Compound L) were found to be capable of disrupting the binding of Ku to DNA as well as the activation of DNA-PK$_{CS}$, thereby effectively blocking the first two critical steps of the NHEJ process. Excitingly, both compounds proved to synergistically sensitize human glioblastoma multiforme (GBM) cells to RT.

Additional experiments conducted during the course of developing embodiments for the present invention further identified the following compounds capable of disrupting the binding of Ku70/80 to DNA substrates and/or impairing Ku-dependent activation of DNA-PK$_{CS}$:

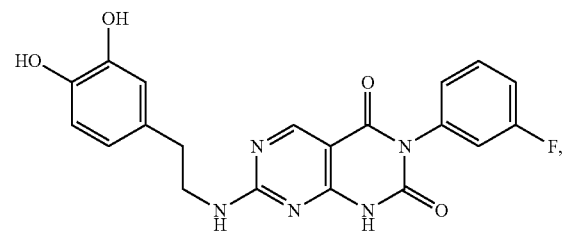

Effectively, such research yields the first published small molecule compounds with Ku70/80-inhibitory activity. Such structures of the identified active compounds can serve as the basis for a focused hit-to-lead research effort, aimed at designing a first generation of high-potency anti-cancer drugs based on inhibiting the central component of NHEJ. Such drugs would be applicable as single modality treatments following a synthetic lethality approach for NHEJ-dependent tumors, or as sensitizing drugs to be used in combination with RT or genotoxic chemotherapy.

Accordingly, provided herein are methods for treating subjects having conditions involving Ku70/80 activity. In particular, the invention relates to small-molecules which function as inhibitors of Ku70/80 protein and the non-homologous end-joining (NHEJ) pathway, and their use as therapeutics for the treatment of cancer and other diseases.

The invention further relates to methods of treating, ameliorating, or preventing disorders in a patient, such as those that are responsive to induction of DSBs and the cellular effects thereof, comprising administering to the patient a compound of the invention as monotherapy or concurrent with additional agent(s), e.g., an inducer of DSBs. Such disorders include those characterized by a dysregulation of DNA repair, cell death mechanisms, and cell cycle arrest mechanisms and those characterized by the proliferation of cells expressing an aberrant Ku70/80 profile and/or NHEJ pathway related activity.

In certain embodiments, the following compounds are provided as capable of disrupting the binding of Ku70/80 to DNA substrates, and/or capable of inhibiting Ku70/80 activity, and/or capable of rendering cancer cells as a population more susceptible to the cell death-inducing activity of cancer therapeutic drugs or radiation therapies, and/or capable of inhibiting the NHEJ pathway related activity, and/or impairing Ku-dependent activation of DNA-PK$_{CS}$, and as such, serve as therapeutics for the treatment of cancer and other diseases:

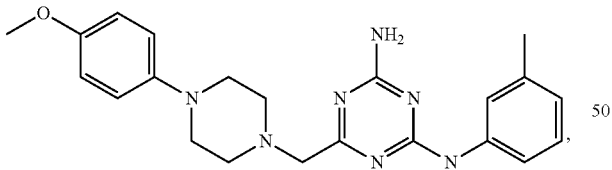

(Compound C and structures similar to Compound C)

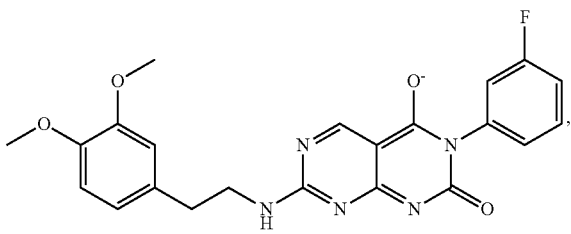

(Compound L and structures similar to Compound L)

-continued

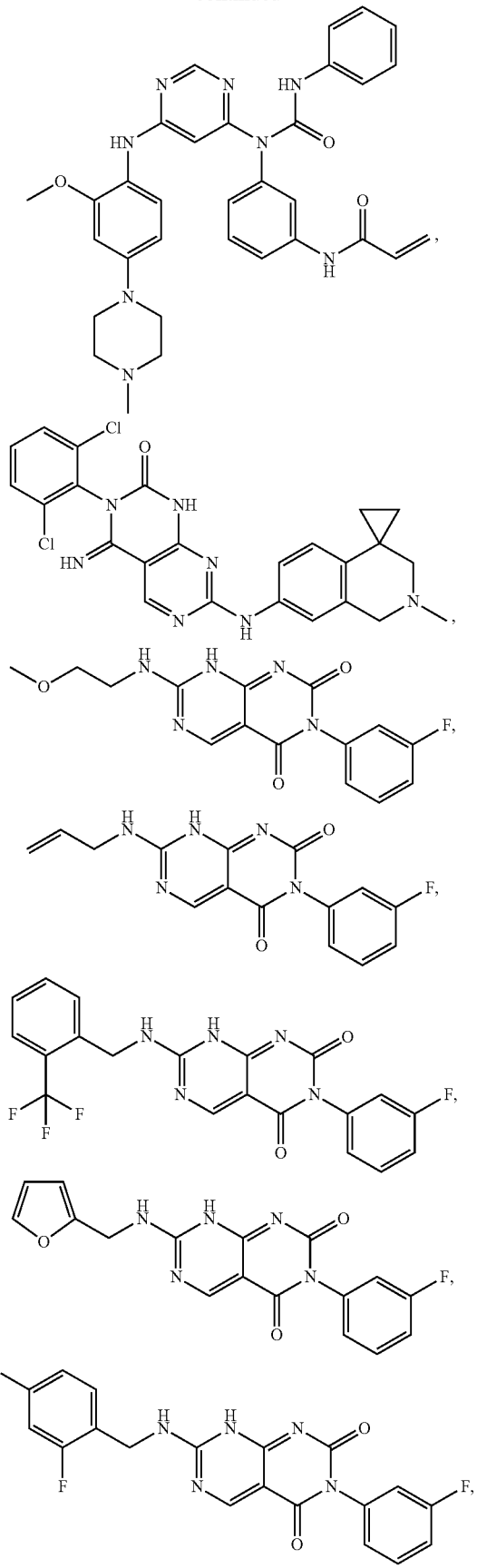

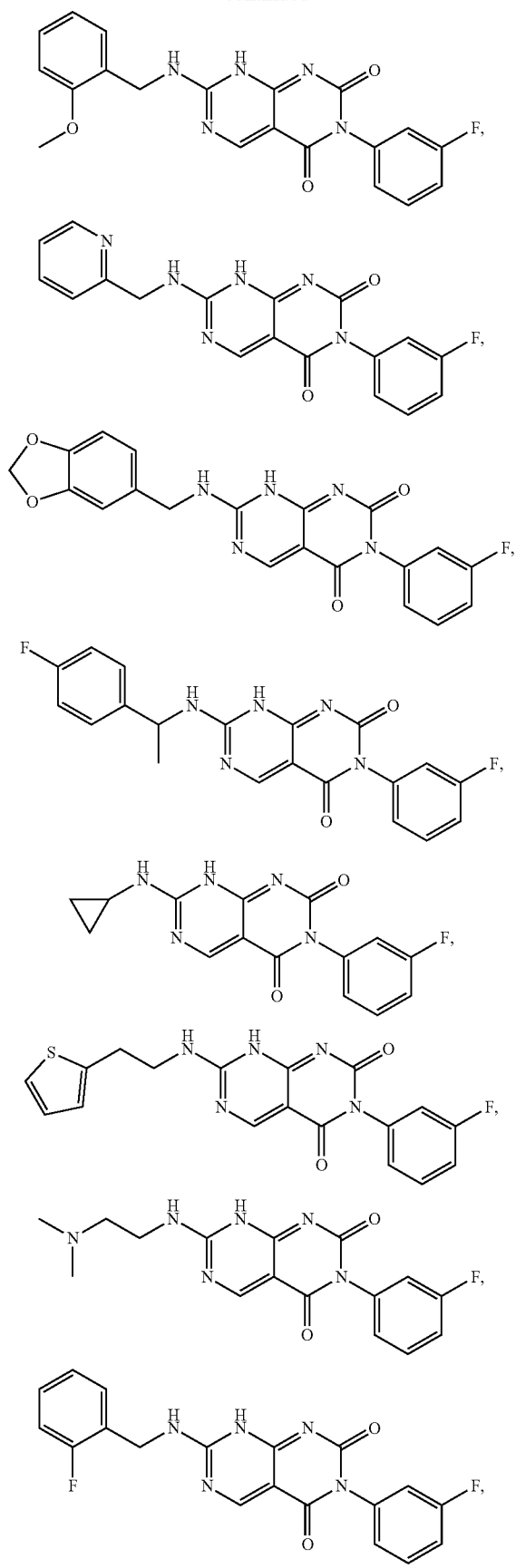
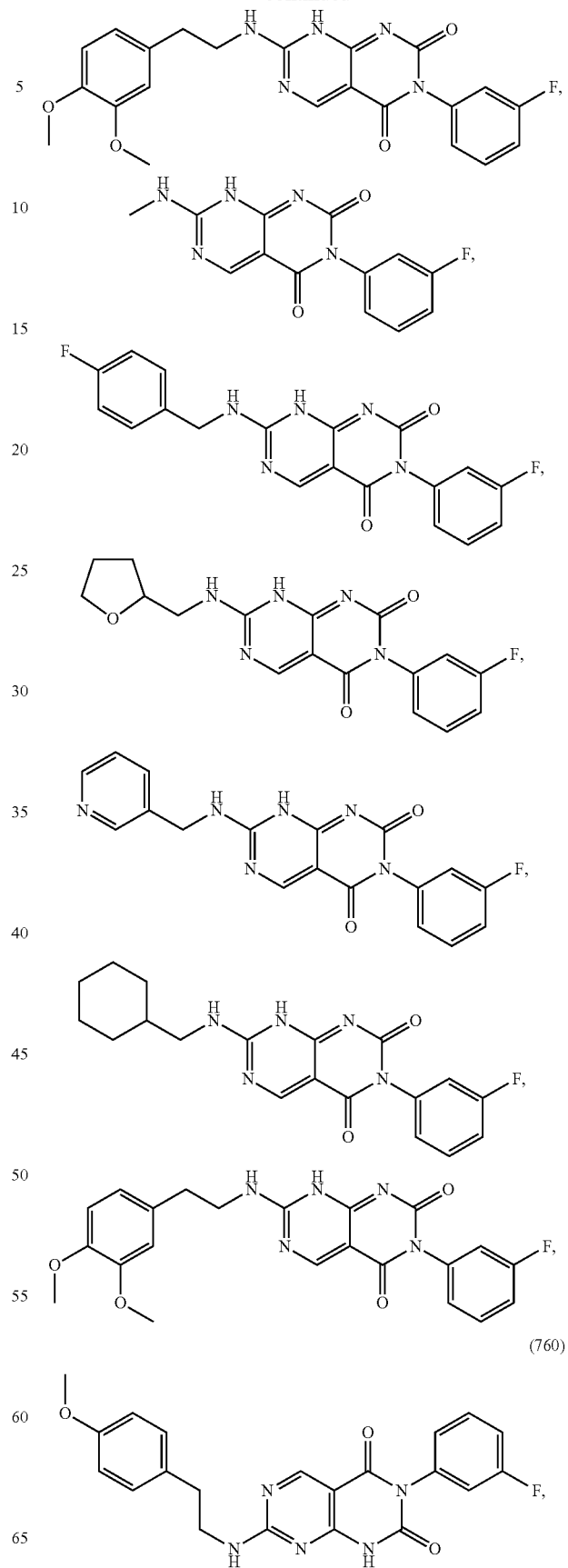

(761)
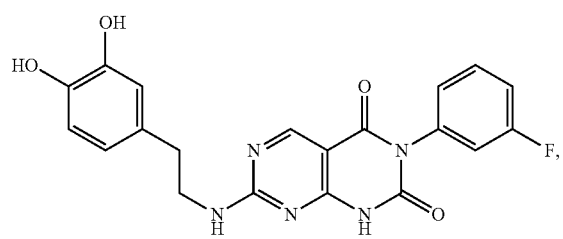
(762)
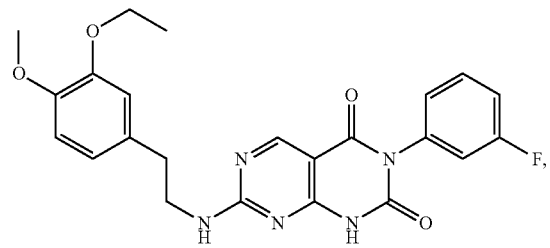
(763)
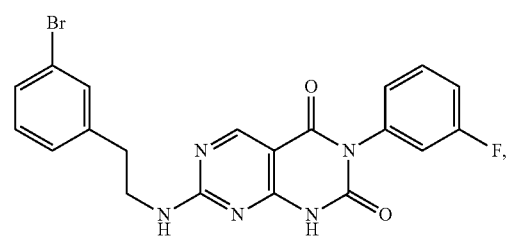
(764)
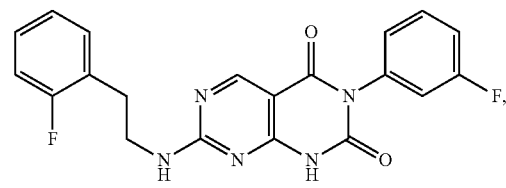
(765)
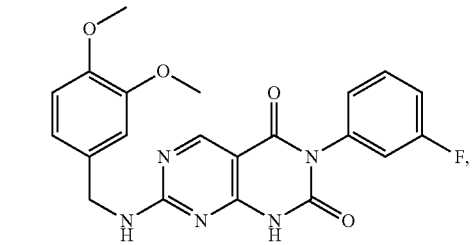
(766)
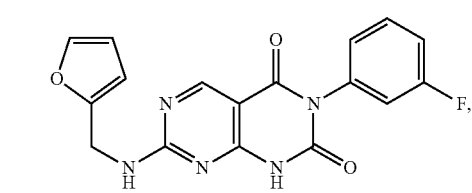
(767)
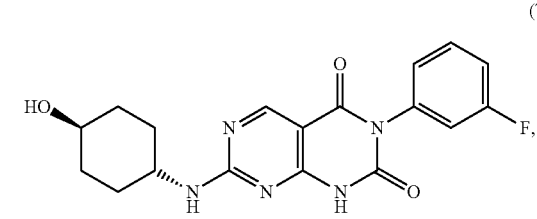
(788)
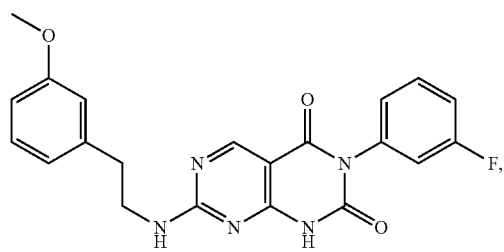
(789)
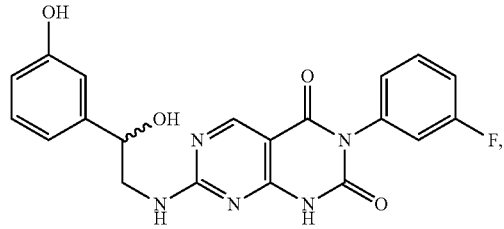
(790)
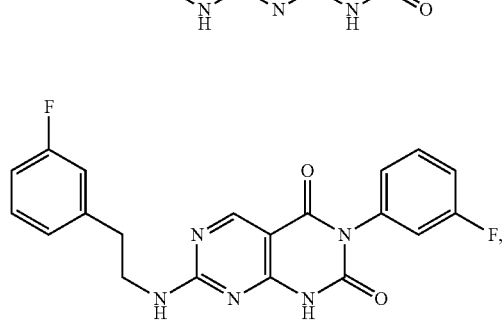
(791)
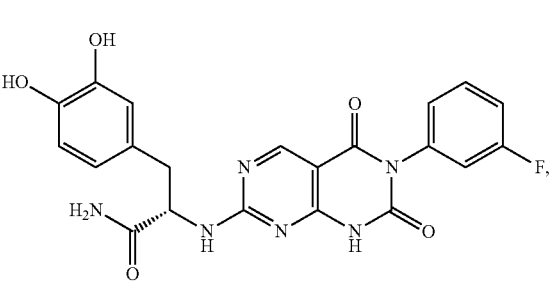
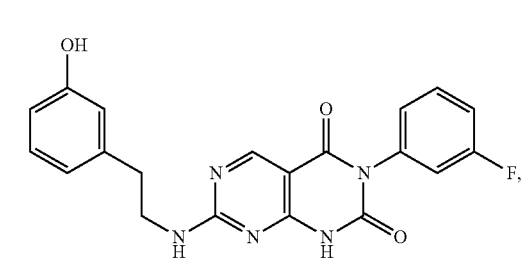

-continued

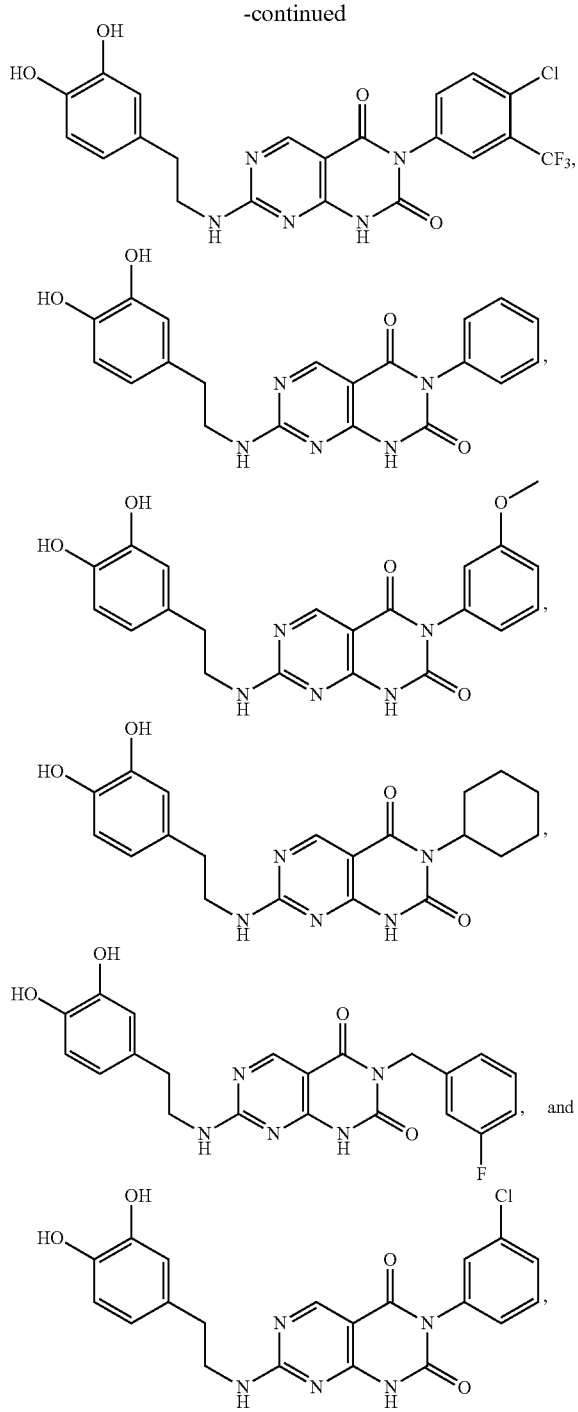

or a pharmaceutically acceptable salt, solvate, or prodrug thereof.

In a particular embodiment, the present invention provides compounds capable of inhibiting Ku70/80 activity, including pharmaceutically acceptable salts, solvates, and/or prodrugs thereof. In a particular embodiment, the present invention provides compounds capable of preventing engagement of Ku70/80 with DNA, including pharmaceutically acceptable salts, solvates, and/or prodrugs thereof. In a particular embodiment, the present invention provides compounds capable of rendering cancer cells as a population more susceptible to the cell death-inducing activity of cancer therapeutic drugs or radiation therapies, including pharmaceutically acceptable salts, solvates, and/or prodrugs thereof. In a particular embodiment, the present invention provides compounds capable of inhibiting the NHEJ pathway related activity, including pharmaceutically acceptable salts, solvates, and/or prodrugs thereof.

An important aspect of the present invention is that compounds of the invention render cancer cells as a population more susceptible to the cell death-inducing activity of cancer therapeutic drugs or radiation therapies, and/or drugs capable of impairing DSB repair through inhibition of NHEJ or Homologous Recombination related activities. Therefore, it is contemplated that these compounds sensitize cells to induction of growth inhibition, cell cycle arrest and/or cell death, including cells that are resistant to such inducing stimuli. In one embodiment, the inhibitors can be used to induce apoptosis in cells comprising functional Ku70/80 and Ku70/80-dependent proteins.

In some embodiments, the compositions and methods of the present invention are used to treat diseased cells, tissues, organs, or pathological conditions and/or disease states in an animal (e.g., a mammalian patient including, but not limited to, humans and veterinary animals). In this regard, various diseases and pathologies are amenable to treatment or prophylaxis using the present methods and compositions. A non-limiting exemplary list of these diseases and conditions includes, but is not limited to, glioblastoma, pancreatic cancer, breast cancer, prostate cancer, lymphoma, skin cancer, colon cancer, melanoma, malignant melanoma, ovarian cancer, brain cancer, primary brain carcinoma, head-neck cancer, glioma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma, and the like, T and B cell mediated autoimmune diseases; inflammatory diseases; infections; hyperproliferative diseases; AIDS; degenerative conditions, vascular diseases, and the like. In some embodiments, the cancer cells being treated are metastatic. In other embodiments, the cancer cells being treated are resistant to anticancer agents. In other embodiments, the disorder is any disorder having cells having aberrant Ku70/80 activity, and/or aberrant NHEJ pathway related activity. In some embodiments, the disorder is any type of solid cancer. In some embodiments, the disorder is any type of hematologic cancer.

Some embodiments of the present invention provide methods for administering an effective amount of a compound of the invention and at least one additional therapeutic agent (including, but not limited to, chemotherapeutic antineoplastics, apoptosis-modulating agents, antimicrobials, antivirals, antifungals, and anti-inflammatory agents)

and/or therapeutic technique (e.g., surgical intervention, and/or radiotherapies). In a particular embodiment, the additional therapeutic agent(s) is an anticancer agent. In a particular embodiment, the additional therapeutic agent(s) is radiation therapy.

A number of suitable anticancer agents are contemplated for use in the methods of the present invention. Indeed, the present invention contemplates, but is not limited to, administration of numerous anticancer agents such as: agents that induce cell death (e.g. apoptosis); DSB-inducing compounds; DSB repair-inhibiting compounds; radio-mimetic compounds; polynucleotides (e.g., anti-sense, ribozymes, siRNA); polypeptides (e.g., enzymes and antibodies); biological mimetics; alkaloids; alkylating agents; antitumor antibiotics; antimetabolites; hormones; platinum compounds; monoclonal or polyclonal antibodies (e.g., antibodies conjugated with anticancer drugs, toxins, defensins), toxins; radionuclides; biological response modifiers (e.g., interferons (e.g., IFN-α) and interleukins (e.g., IL-2)); adoptive immunotherapy agents; hematopoietic growth factors; agents that induce tumor cell differentiation (e.g., all-trans-retinoic acid); gene therapy reagents (e.g., antisense therapy reagents and nucleotides); tumor vaccines; angiogenesis inhibitors; proteosome inhibitors: NF-KB modulators; anti-CDK compounds; HDAC inhibitors; and the like. Numerous other examples of chemotherapeutic compounds and anti-cancer therapies suitable for co-administration with the disclosed compounds are known to those skilled in the art.

In certain embodiments, anticancer agents comprise agents that induce or stimulate apoptosis. Agents that induce apoptosis include, but are not limited to, radiation (e.g., X-rays, gamma rays, UV); tumor necrosis factor (TNF)-related factors (e.g., TNF family receptor proteins, TNF family ligands, TRAIL, antibodies to TRAIL-R1 or TRAIL-R2); kinase inhibitors (e.g., epidermal growth factor receptor (EGFR) kinase inhibitor, vascular growth factor receptor (VGFR) kinase inhibitor, fibroblast growth factor receptor (FGFR) kinase inhibitor, platelet-derived growth factor receptor (PDGFR) kinase inhibitor, and Bcr-Abl kinase inhibitors (such as GLEEVEC)); antisense molecules; antibodies (e.g., HERCEPTIN, RITUXAN, ZEVALIN, and AVASTIN); Immune checkpoint modulators (anti-CTLA-4, anti-PD-1, anti-PDL-1, anti-OX40 and the like. anti-estrogens (e.g., raloxifene and tamoxifen); anti-androgens (e.g., flutamide, bicalutamide, finasteride, aminoglutethamide, ketoconazole, and corticosteroids); cyclooxygenase 2 (COX-2) inhibitors (e.g., celecoxib, meloxicam, NS-398, and non-steroidal anti-inflammatory drugs (NSAIDs)); anti-inflammatory drugs (e.g., butazolidin, DECADRON, DELTASONE, dexamethasone, dexamethasone intensol, DEXONE, HEXADROL, hydroxychloroquine, METICORTEN, ORADEXON, ORASONE, oxyphenbutazone, PEDIAPRED, phenylbutazone, PLAQUENIL, prednisolone, prednisone, PRELONE, and TANDEARIL); and cancer chemotherapeutic drugs (e.g., irinotecan (CAMPTOSAR), CPT-11, fludarabine (FLUDARA), dacarbazine (DTIC), dexamethasone, mitoxantrone, MYLOTARG, VP-16, cisplatin, carboplatin, oxaliplatin, 5-FU, doxorubicin, gemcitabine, bortezomib, gefitinib, bevacizumab, TAXOTERE or TAXOL); cellular signaling molecules; ceramides and cytokines; staurosporine, and the like.

In still other embodiments, the compositions and methods of the present invention provide a compound of the invention and at least one anti-hyperproliferative or antineoplastic agent selected from alkylating agents, antimetabolites, and natural products (e.g., herbs and other plant and/or animal derived compounds).

Alkylating agents suitable for use in the present compositions and methods include, but are not limited to: 1) nitrogen mustards (e.g., mechlorethamine, cyclophosphamide, ifosfamide, melphalan (L-sarcolysin); and chlorambucil); 2) ethylenimines and methylmelamines (e.g., hexamethylmelamine and thiotepa); 3) alkyl sulfonates (e.g., busulfan); 4) nitrosoureas (e.g., carmustine (BCNU); lomustine (CCNU); semustine (methyl-CCNU); and streptozocin (streptozotocin)); and 5) triazenes (e.g., dacarbazine (DTIC; dimethyltriazenoimid-azolecarboxamide).

In some embodiments, antimetabolites suitable for use in the present compositions and methods include, but are not limited to: 1) folic acid analogs (e.g., methotrexate (amethopterin)); 2) pyrimidine analogs (e.g., fluorouracil (5-fluorouracil; 5-FU), floxuridine (fluorode-oxyuridine; FudR), and cytarabine (cytosine arabinoside)); and 3) purine analogs (e.g., mercaptopurine (6-mercaptopurine; 6-MP), thioguanine (6-thioguanine; TG), and pentostatin (2'-deoxycoformycin)).

In still further embodiments, chemotherapeutic agents suitable for use in the compositions and methods of the present invention include, but are not limited to: 1) vinca alkaloids (e.g., vinblastine (VLB), vincristine); 2) epipodophyllotoxins (e.g., etoposide and teniposide); 3) antibiotics (e.g., dactinomycin (actinomycin D), daunorubicin (daunomycin; rubidomycin), doxorubicin, bleomycin, plicamycin (mithramycin), and mitomycin (mitomycin C)); 4) enzymes (e.g., L-asparaginase); 5) biological response modifiers (e.g., interferon-alfa); 6) platinum coordinating complexes (e.g., cisplatin (cis-DDP) and carboplatin); 7) anthracenediones (e.g., mitoxantrone); 8) substituted ureas (e.g., hydroxyurea); 9) methylhydrazine derivatives (e.g., procarbazine (N-methylhydrazine; MIH)); 10) adrenocortical suppressants (e.g., mitotane (o,p'-DDD) and aminoglutethimide); 11) adrenocorticosteroids (e.g., prednisone); 12) progestins (e.g., hydroxyprogesterone caproate, medroxyprogesterone acetate, and megestrol acetate); 13) estrogens (e.g., diethylstilbestrol and ethinyl estradiol); 14) antiestrogens (e.g., tamoxifen); 15) androgens (e.g., testosterone propionate and fluoxymesterone); 16) antiandrogens (e.g., flutamide): and 17) gonadotropin-releasing hormone analogs (e.g., leuprolide).

Any oncolytic agent that is routinely used in a cancer therapy context finds use in the compositions and methods of the present invention. For example, the U.S. Food and Drug Administration maintains a formulary of oncolytic agents approved for use in the United States. International counterpart agencies to the U.S.F.D.A. maintain similar formularies. Table 2 provides a list of exemplary antineoplastic agents approved for use in the U.S. Those skilled in the art will appreciate that the "product labels" required on all U.S. approved chemotherapeutics describe approved indications, dosing information, toxicity data, and the like, for the exemplary agents.

TABLE 2

| | | |
|---|---|---|
| Aldesleukin (des-alanyl-1, serine-125 human interleukin-2) | Proleukin | Chiron Corp., Emeryville, CA |
| Alemtuzumab (IgG1κ anti CD52 antibody) | Campath | Millennium and ILEX Partners, LP, Cambridge, MA |
| Alitretinoin (9-cis-retinoic acid) | Panretin | Ligand Pharmaceuticals, Inc., San Diego CA |

TABLE 2-continued

| Drug | Brand | Manufacturer |
|---|---|---|
| Allopurinol (1,5-dihydro-4 H-pyrazolo[3,4-d]pyrimidin-4-one monosodium salt) | Zyloprim | GlaxoSmithKline, Research Triangle Park, NC |
| Altretamine (N,N,N',N',N'',N'',-hexamethyl-1,3,5-triazine-2,4,6-triamine) | Hexalen | US Bioscience, West Conshohocken, PA |
| Amifostine (ethanethiol, 2-[(3-aminopropyl)amino]-, dihydrogen phosphate (ester)) | Ethyol | US Bioscience |
| Anastrozole (1,3-Benzenediacetonitrile, a,a,a',a'-tetramethyl-5-(1H-1,2,4-triazol-1-ylmethyl)) | Arimidex | AstraZeneca Pharmaceuticals, LP, Wilmington, DE |
| Arsenic trioxide | Trisenox | Cell Therapeutic, Inc., Seattle, WA |
| Asparaginase (L-asparagine amidohydrolase, type EC-2) | Elspar | Merck & Co., Inc., Whitehouse Station, NJ |
| BCG Live (lyophilized preparation of an attenuated strain of *Mycobacterium bovis* (*Bacillus* Calmette-Gukin [BCG], substrain Montreal) | TICE BCG | Organon Teknika, Corp., Durham, NC |
| bexarotene capsules (4-[1-(5,6,7,8-tetrahydro-3,5,5,8,8-pentamethyl-2-napthalenyl) ethenyl] benzoic acid) | Targretin | Ligand Pharmaceuticals |
| bexarotene gel | Targretin | Ligand Pharmaceuticals |
| Bleomycin (cytotoxic glycopeptide antibiotics produced by *Streptomyces verticillus*; bleomycin $A_2$ and bleomycin $B_2$) | Blenoxane | Bristol-Myers Squibb Co., NY, NY |
| Capecitabine (5'-deoxy-5-fluoro-N-[(pentyloxy)carbonyl]-cytidine) | Xeloda | Roche |
| Carboplatin (platinum, diammine [1,1-cyclobutanedicarboxylato(2-)-0,0']-, (SP-4-2)) | Paraplatin | Bristol-Myers Squibb |
| Carmustine (1,3-bis(2-chloroethyl)-1-nitrosourea) | BCNU, BiCNU | Bristol-Myers Squibb |
| Carmustine with Polifeprosan 20 Implant | Gliadel Wafer | Guilford Pharmaceuticals, Inc., Baltimore, MD |
| Celecoxib (as 4-[5-(4-methylphenyl)-3-(trifluoromethyl)-1H-pyrazol-1-yl] benzenesulfonamide) | Celebrex | Searle Pharmaceuticals, England |
| Chlorambucil (4-[bis(2chloroethyl)amino]benzenebutanoic acid) | Leukeran | GlaxoSmithKline |
| Cisplatin ($PtCl_2H_6N_2$) | Platinol | Bristol-Myers Squibb |
| Cladribine (2-chloro-2'-deoxy-b-D-adenosine) | Leustatin, 2-CdA | R. W. Johnson Pharmaceutical Research Institute, Raritan, NJ |
| Cyclophosphamide (2-[bis(2-chloroethyl)amino] tetrahydro-2H-13,2-oxazaphosphorine 2-oxide monohydrate) | Cytoxan, Neosar | Bristol-Myers Squibb |
| Cytarabine (1-b-D-Arabinofuranosylcytosine, $C_9H_{13}N_3O_5$) | Cytosar-U | Pharmacia & Upjohn Company |
| cytarabine liposomal | DepoCyt | Skye Pharmaceuticals, Inc., San Diego, CA |
| Dacarbazine (5-(3,3-dimethyl-1-triazeno)-imidazole-4-carboxamide (DTIC)) | DTIC-Dome | Bayer AG, Leverkusen, Germany |
| Dactinomycin, actinomycin D (actinomycin produced by *Streptomyces parvullus*, $C_{62}H_{86}N_{12}O_{16}$) | Cosmegen | Merck |
| Darbepoetin alfa (recombinant peptide) | Aranesp | Amgen, Inc., Thousand Oaks, CA |
| daunorubicin liposomal ((8S-cis)-8-acetyl-10-[(3-amino-2,3,6-trideoxy-á-L-lyxo-hexopyranosyl)oxy]-7,8,9,10-tetrahydro-6,8,11-trihydroxy-1-methoxy-5,12-naphthacenedione hydrochloride) | DanuoXome | Nexstar Pharmaceuticals, Inc., Boulder, CO |
| Daunorubicin HCl, daunomycin ((1 S,3 S)-3-Acetyl-1,2,3,4,6,11-hexahydro-3,5,12-trihydroxy-10-methoxy-6,11-dioxo-1-naphthacenyl 3-amino-2,3,6-trideoxy-(alpha)-L-lyxo-hexopyranoside hydrochloride) | Cerubidine | Wyeth Ayerst, Madison, NJ |
| Denileukin diftitox (recombinant peptide) | Ontak | Seragen, Inc., Hopkinton, MA |
| Dexrazoxane ((S)-4,4'-(1-methyl-1,2-ethanediyl)bis-2,6-piperazinedione) | Zinecard | Pharmacia & Upjohn Company |

TABLE 2-continued

| | | |
|---|---|---|
| Docetaxel<br>((2R,3S)-N-carboxy-3-phenylisoserine, N-tert-butyl ester,<br>13-ester with 5b-20-epoxy-12a,4,7b,10b,13a-<br>hexahydroxytax- 11-en-9-one 4-acetate 2-benzoate,<br>trihydrate) | Taxotere | Aventis Pharmaceuticals, Inc.,<br>Bridgewater, NJ |
| Doxorubicin HCl<br>(8S,10S)-10-[(3-amino-2,3,6-trideoxy-a-L-lyxo-<br>hexopyranosyl)oxy] -8-glycolyl-7,8,9,10-tetrahydro-<br>6,8,11-trihydroxy-1-methoxy-5,12-naphthacenedione<br>hydrochloride) | Adriamycin, Rubex | Pharmacia & Upjohn<br>Company |
| doxorubicin | Adriamycin PFS<br>Intravenous injection | Pharmacia & Upjohn<br>Company |
| doxorubicin liposomal | Doxil | Sequus Pharmaceuticals, Inc.,<br>Menlo park, CA |
| dromostanolone propionate<br>(17b-Hydroxy-2a-methyl-5a-androstan-3-one propionate) | Dromostanolone | Eli Lilly & Company,<br>Indianapolis, IN |
| dromostanolone propionate | Masterone injection | Syntex, Corp., Palo Alto, CA |
| Elliott's B Solution | Elliott's B Solution | Orphan Medical, Inc |
| Epirubicin<br>((8S-cis)-10-[(3-amino-2,3,6-trideoxy-a-L-arabino-<br>hexopyranosyl)oxy]-7,8,9,10-tetrahydro-6,8,11-<br>trihydroxy-8-(hydroxyacetyl)-1-methoxy-5,12-<br>naphthacenedione hydrochloride) | Ellence | Pharmacia & Upjohn<br>Company |
| Epoetin alfa<br>(recombinant peptide) | Epogen | Amgen, Inc |
| Estramustine<br>(estra-1,3,5(10)-triene-3,17-diol(17(beta))-, 3-[bis(2-<br>chloroethyl)carbamate] 17-(dihydrogen phosphate),<br>disodium salt, monohydrate, or estradiol 3-[bis(2-<br>chloroethyl)carbamate] 17-(dihydrogen phosphate),<br>disodium salt, monohydrate) | Emcyt | Pharmacia & Upjohn<br>Company |
| Etoposide phosphate<br>(4'-Demethylepipodophyllotoxin 9-[4,6-O-(R)-<br>ethylidene-(beta)-D-glucopyranoside], 4'-(dihydrogen<br>phosphate)) | Etopophos | Bristol-Myers Squibb |
| etoposide, VP-16<br>(4'-demethylepipodophyllotoxin 9-[4,6-0-(R)-ethylidene-<br>(beta)-D-glucopyranoside]) | Vepesid | Bristol-Myers Squibb |
| Exemestane<br>(6-methylenandrosta-1,4-diene-3,17-dione) | Aromasin | Pharmacia & Upjohn<br>Company |
| Filgrastim<br>(r-metHuG-CSF) | Neupogen | Amgen, Inc |
| floxuridine (intraarterial)<br>(2'-deoxy-5-fluorouridine) | FUDR | Roche |
| Fludarabine<br>(fluorinated nucleotide analog of the antiviral agent<br>vidarabine, 9-b-D-arabinofuranosyladenine (ara-A)) | Fludara | Berlex Laboratories, Inc.,<br>Cedar Knolls, NJ |
| Fluorouracil, 5-FU<br>(5-fluoro-2,4(1H,3H)-pyrimidinedione) | Adrucil | ICN Pharmaceuticals, Inc.,<br>Humacao, Puerto Rico |
| Fulvestrant<br>(7-alpha-[9-(4,4,5,5,5-penta fluoropentylsulphinyl)<br>nonyl]estra-1,3,5-(10)-triene-3,17-beta-diol) | Faslodex | IPR Pharmaceuticals,<br>Guayama, Puerto Rico |
| Gemcitabine<br>(2'-deoxy-2', 2'-difluorocytidine monohydrochloride<br>(b-isomer)) | Gemzar | Eli Lilly |
| Gemtuzumab Ozogamicin<br>(anti-CD33 hP67.6) | Mylotarg | Wyeth Ayerst |
| Goserelin acetate | Zoladex Implant | AstraZeneca Pharmaceuticals |
| Hydroxyurea | Hydrea | Bristol-Myers Squibb |
| Ibritumomab Tiuxetan<br>(immunoconjugate resulting from a thiourea covalent<br>bond between the monoclonal antibody Ibritumomab and<br>the linker-chelator tiuxetan [N-[2-<br>bis(carboxymethyl)amino]-3-(p-isothiocyanatophenyl)-<br>propyl]-[N-[2-bis(carboxymethyl)amino]-2-(methyl) -<br>ethyl]glycine) | Zevalin | Biogen IDEC, Inc.,<br>Cambridge MA |
| Idarubicin<br>(5, 12-Naphthacenedione, 9-acetyl-7-[(3-amino-2,3,6-<br>trideoxy-(alpha)-L- lyxo -hexopyranosyl)oxy]-7,8,9,10-<br>tetrahydro-6,9,11-trihydroxyhydrochloride, (7S- cis)) | Idamycin | Pharmacia & Upjohn<br>Company |
| Ifosfamide<br>(3-(2-chloroethyl)-2-[(2-chloroethyl)amino]tetrahydro-<br>2H-1,3,2-oxazaphosphorine 2-oxide) | IFEX | Bristol-Myers Squibb |
| Imatinib Mesilate<br>(4-[(4-Methyl-1-piperazinyl)methyl]-N-[4-methyl-3-[[4-<br>(3-pyridinyl)-2-pyrimidinyl]amino]-phenyl]benzamide<br>methanesulfonate) | Gleevec | Novartis AG, Basel,<br>Switzerland |
| Interferon alfa-2a<br>(recombinant peptide) | Roferon-A | Hoffmann-La Roche, Inc.,<br>Nutley, NJ |

TABLE 2-continued

| | | |
|---|---|---|
| Interferon alfa-2b (recombinant peptide) | Intron A (Lyophilized Betaseron) | Schering AG, Berlin, Germany |
| Irinotecan HCl ((4S)-4,11-diethyl-4-hydroxy-9-[(4-piperidinopiperidino)carbonyloxy]-1H-pyrano[3',4': 6,7] indolizino[1,2-b] quinoline-3,14(4H, 12H) dione hydrochloride trihydrate) | Camptosar | Pharmacia & Upjohn Company |
| Letrozole (4,4'-(1H-1,2,4-Triazol-1-ylmethylene) dibenzonitrile) | Femara | Novartis |
| Leucovorin (L-Glutamic acid, N[4[[(2amino-5-formyl-1,4,5,6,7,8 hexahydro4oxo6-pteridinyl)methyl]amino]benzoyl], calcium salt (1:1)) | Wellcovorin, Leucovorin | Immunex, Corp., Seattle, WA |
| Levamisole HCl ((−)-(S)-2,3,5, 6-tetrahydro-6-phenylimidazo [2,1-b] thiazole monohydrochloride $C_{11}H_{12}N_2S \cdot HCl$) | Ergamisol | Janssen Research Foundation, Titusville, NJ |
| Lomustine (1-(2-chloro-ethyl)-3-cyclohexyl-1-nitrosourea) | CeeNU | Bristol-Myers Squibb |
| Mechlorethamine, nitrogen mustard (2-chloro-N-(2-chloroethyl)-N-methylethanamine hydrochloride) | Mustargen | Merck |
| Megestrol acetate 17α(acetyloxy)- 6- methylpregna- 4,6- diene-3,20- dione | Megace | Bristol-Myers Squibb |
| Melphalan, L-PAM (4-[bis(2-chloroethyl) amino]-L-phenylalanine) | Alkeran | GlaxoSmithKline |
| Mercaptopurine, 6-MP (1,7-dihydro-6 H -purine-6-thione monohydrate) | Purinethol | GlaxoSmithKline |
| Mesna (sodium 2-mercaptoethane sulfonate) | Mesnex | Asta Medica |
| Methotrexate (N-[4-[[(2,4-diamino-6-pteridinyl)methyl]methylamino]benzoyl]-L-glutamic acid) | Methotrexate | Lederle Laboratories |
| Methoxsalen (9-methoxy-7H-furo[3,2-g][1]-benzopyran-7-one) | Uvadex | Therakos, Inc., Way Exton, Pa |
| Mitomycin C | Mutamycin | Bristol-Myers Squibb |
| mitomycin C | Mitozytrex | SuperGen, Inc., Dublin, CA |
| Mitotane (1,1-dichloro-2-(o-chlorophenyl)-2-(p-chlorophenyl) ethane) | Lysodren | Bristol-Myers Squibb |
| Mitoxantrone (1,4-dihydroxy-5,8-bis[[2- [(2-hydroxyethyl)amino]ethyl]amino]-9,10-anthracenedione dihydrochloride) | Novantrone | Immunex Corporation |
| Nandrolone phenpropionate | Durabolin-50 | Organon, Inc., West Orange, NJ |
| Nofetumomab | Verluma | Boehringer Ingelheim Pharma KG, Germany |
| Oprelvekin (IL-11) | Neumega | Genetics Institute, Inc., Alexandria, VA |
| Oxaliplatin (cis-[(1R,2R)-1,2-cyclohexanediamine-N,N'] [oxalato(2-)-O,O'] platinum) | Eloxatin | Sanofi Synthelabo, Inc., NY, NY |
| Paclitaxel (5β, 20-Epoxy-1,2a, 4,7β, 10β, 13a-hexahydroxytax-11-en-9-one 4,10-diacetate 2-benzoate 13-ester with (2R, 3 S)-N-benzoyl-3-phenylisoserine) | TAXOL | Bristol-Myers Squibb |
| Pamidronate (phosphonic acid (3-amino-1-hydroxypropylidene) bis-, disodium salt, pentahydrate, (APD)) | Aredia | Novartis |
| Pegademase ((monomethoxypolyethylene glycol succinimidyl) 11 - 17 - adenosine deaminase) | Adagen (Pegademase Bovine) | Enzon Pharmaceuticals, Inc., Bridgewater, NJ |
| Pegaspargase (monomethoxypolyethylene glycol succinimidyl L-asparaginase) | Oncaspar | Enzon |
| Pegfilgrastim (covalent conjugate of recombinant methionyl human G-CSF (Filgrastim) and monomethoxypolyethylene glycol) | Neulasta | Amgen, Inc |
| Pentostatin | Nipent | Parke-Davis Pharmaceutical Co., Rockville, MD |
| Pipobroman | Vercyte | Abbott Laboratories, Abbott Park, IL |
| Plicamycin, Mithramycin (antibiotic produced by *Streptomyces plicatus*) | Mithracin | Pfizer, Inc., NY, NY |
| Porfimer sodium | Photofrin | QLT Phototherapeutics, Inc., Vancouver, Canada |
| Procarbazine (N-isopropyl-μ-(2-methylhydrazino)-p-toluamide monohydrochloride) | Matulane | Sigma Tau Pharmaceuticals, Inc., Gaithersburg, MD |

TABLE 2-continued

| | | |
|---|---|---|
| Quinacrine (6-chloro-9-(1-methyl-4-diethyl-amine) butylamino-2-methoxyacridine) | Atabrine | Abbott Labs |
| Rasburicase (recombinant peptide) | Elitek | Sanofi-Synthelabo, Inc., |
| Rituximab (recombinant anti-CD20 antibody) | Rituxan | Genentech, Inc., South San Francisco, CA |
| Sargramostim (recombinant peptide) | Prokine | Immunex Corp |
| Streptozocin (streptozocin 2-deoxy - 2 - [[(methylnitrosoamino)carbonyl]amino] - a(and b) - D - glucopyranose and 220 mg citric acid anhydrous) | Zanosar | Pharmacia & Upjohn Company |
| Talc ($Mg_3Si_4O_{10}$ $(OH)_2$) | Sclerosol | Bryan, Corp., Woburn, MA |
| Tamoxifen ((Z)2-[4-(1,2-diphenyl-1-butenyl) phenoxy]-N,N-dimethylethanamine 2-hydroxy-1,2,3-propanetricarboxylate (1:1)) | Nolvadex | AstraZeneca Pharmaceuticals |
| Temozolomide (3,4-dihydro-3-methyl-4-oxoimidazo[5,1-d]-as-tetrazine-8-carboxamide) | Temodar | Schering |
| teniposide, VM-26 (4'-demethylepipodophyllotoxin 9-[4,6-0-(R)-2-thenylidene-(beta)-D-glucopyranoside]) | Vumon | Bristol-Myers Squibb |
| Testolactone (13-hydroxy-3-oxo-13,17-secoandrosta-1,4-dien-17-oic acid [dgr]-lactone) | Teslac | Bristol-Myers Squibb |
| Thioguanine, 6-TG (2-amino-1,7-dihydro-6 H - purine-6-thione) | Thioguanine | GlaxoSmithKline |
| Thiotepa (Aziridine, 1,1',1''-phosphinothioylidynetris-, or Tris (1-aziridinyl) phosphine sulfide) | Thioplex | Immunex Corporation |
| Topotecan HCl ((S)-10-[(dimethylamino) methyl]-4-ethyl-4,9-dihydroxy-1H-pyrano[3',4': 6,7] indolizino [1,2-b] quinoline-3,14-4H,12H)-dione monohydrochloride) | Hycamtin | GlaxoSmithKline |
| Toremifene (2-(p-[(Z)-4-chloro-1,2-diphenyl-1-butenyl]-phenoxy)-N,N-dimethylethylamine citrate (1:1)) | Fareston | Roberts Pharmaceutical Corp., Eatontown, NJ |
| Tositumomab, I 131 Tositumomab (recombinant murine immunotherapeutic monoclonal $IgG_{2a}$ lambda anti-CD20 antibody (I 131 is a radioimmunotherapeutic antibody)) | Bexxar | Corixa Corp., Seattle, WA |
| Trastuzumab (recombinant monoclonal $IgG_1$ kappa anti-HER2 antibody) | Herceptin | Genentech, Inc |
| Tretinoin, ATRA (all-trans retinoic acid) | Vesanoid | Roche |
| Uracil Mustard | Uracil Mustard Capsules | Roberts Labs |
| Valrubicin, N-trifluoroacetyladriamycin-14-valerate ((2S-cis)-2- [1,2,3,4,6,11-hexahydro-2,5,12-trihydroxy-7 methoxy-6,11-dioxo-[[4 2,3,6-trideoxy-3-[(trifluoroacetyl)-amino-α-L-lyxo-hexopyranosyl]oxyl]-2-naphthacenyl]-2-oxoethyl pentanoate) | Valstar | Anthra --> Medeva |
| Vinblastine, Leurocristine ($C_{46}H_{56}N_4O_{10}$•$H_2SO_4$) | Velban | Eli Lilly |
| Vincristine ($C_{46}H_{56}N_4O_{10}$•$H_2SO_4$) | Oncovin | Eli Lilly |
| Vinorelbine (3',4'-didehydro-4'-deoxy-C'-norvincaleukoblastine [R-(R*,R*)-2,3-dihydroxybutanedioate (1:2)(salt)]) | Navelbine | GlaxoSmithKline |
| Zoledronate, Zoledronic acid ((1-Hydroxy-2-imidazol-1-yl-phosphonoethyl) phosphonic acid monohydrate) | Zometa | Novartis |

Anticancer agents further include compounds which have been identified to have anticancer activity. Examples include, but are not limited to, 3-AP, 12-O-tetradecanoyl-phorbol-13-acetate, 17AAG, 852A, ABI-007, ABR-217620, ABT-751, ADI-PEG 20, AE-941, AG-013736, AGRO100, alanosine, AMG 706, antibody G250, antineoplastons, AP23573, apaziquone, APC8015, atiprimod, ATN-161, atrasenten, azacytidine, BB-10901, BCX-1777, bevacizumab, BG00001, bicalutamide, BMS 247550, bortezomib, bryostatin-1, buserelin, calcitriol, CCI-779, CDB-2914, cefixime, cetuximab, CG0070, cilengitide, clofarabine, combretastatin A4 phosphate, CP-675,206, CP-724,714, CpG 7909, curcumin, decitabine, DENSPM, doxercalciferol, E7070, E7389, ecteinascidin 743, efaproxiral, eflornithine, EKB-569, enzastaurin, erlotinib, exisulind, fenretinide, flavopiridol, fludarabine, flutamide, fotemustine, FR901228, G17DT, galiximab, gefitinib, genistein, glufosfamide, GTI-2040, histrelin, HKI-272, homoharringtonine, HSPPC-96, hu14.18-interleukin-2 fusion protein, HuMax-CD4, iloprost, imiquimod, infliximab, interleukin-12, IPI-504, irofulven, ixabepilone, lapatinib, lenalidomide, lestaurtinib, leuprolide, LMB-9 immunotoxin, lonafarnib, luniliximab, mafosfamide, MB07133, MDX-010, MLN2704, monoclonal antibody 3F8, monoclonal antibody J591, motexafin, MS-275, MVA-MUC1-IL2, nilutamide, nitrocamptothecin, nolatrexed dihydrochloride, nolvadex, NS-9, 06-benzylguanine, oblimersen sodium, ONYX-015, oregovomab, OSI-774, panitumumab, paraplatin, PD-0325901, pemetrexed, PHY906, pioglitazone, pirfenidone, pixantrone, PS-341, PSC 833, PXD101, pyrazoloacridine, R115777, RAD001, ranpirnase, rebeccamycin analogue, rhuAngiostatin protein, rhuMab 2C4, rosiglitazone, rubitecan, S-1, S-8184, satraplatin, SB-, 15992, SGN-0010, SGN-40, sorafenib, SR31747A, ST1571, SU011248, suberoylanilide hydroxamic acid, suramin, talabostat, talampanel, tariquidar, temsirolimus, TGFa-PE38 immunotoxin, thalidomide, thymalfasin, tipifarnib, tirapazamine, TLK286, trabectedin, trimetrexate glucuronate, TroVax, UCN-1, valproic acid, vinflunine, VNP40101M, volociximab, vorinostat, VX-680, ZD1839, ZD6474, zileuton, and zosuquidar trihydrochloride.

For a more detailed description of anticancer agents and other therapeutic agents, those skilled in the art are referred to any number of instructive manuals including, but not limited to, the Physician's Desk Reference and to Goodman and Gilman's "Pharmaceutical Basis of Therapeutics" tenth edition, Eds. Hardman et al., 2002.

The present invention provides methods for administering a compound of the invention with radiation therapy. The invention is not limited by the types, amounts, or delivery and administration systems used to deliver the therapeutic dose of radiation to an animal (e.g., human). For example, the animal may receive photon radiotherapy, particle beam radiation therapy, other types of radiotherapies, and combinations thereof. In some embodiments, the radiation is delivered to the animal using a linear accelerator. In still other embodiments, the radiation is delivered using a gamma knife.

The source of radiation can be external or internal to the animal. External radiation therapy is most common and involves directing a beam of high-energy radiation to a tumor site through the skin using, for instance, a linear accelerator. While the beam of radiation is localized to the tumor site, it is nearly impossible to avoid exposure of normal, healthy tissue. However, external radiation is usually well tolerated by animals. Internal radiation therapy involves implanting a radiation-emitting source, such as beads, wires, pellets, capsules, particles, and the like, inside the body at or near the tumor site including the use of delivery systems that specifically target cancer cells (e.g., using particles attached to cancer cell binding ligands). Such implants can be removed following treatment, or left in the body inactive. Types of internal radiation therapy include, but are not limited to, brachytherapy, interstitial irradiation, intracavity irradiation, radioimmunotherapy, and the like.

The animal may optionally receive radiosensitizers (e.g., metronidazole, misonidazole, intra-arterial BUdR, intravenous iododeoxyuridine (IudR), nitroimidazole, 5-substituted-4-nitroimidazoles, 2H-isoindolediones, [[(2-bromoethyl)-amino]methyl]-nitro-1H-imidazole-1-ethanol, nitroaniline derivatives, DNA-affinic hypoxia selective cytotoxins, halogenated DNA ligand, 1,2,4 benzotriazine oxides, 2-nitroimidazole derivatives, fluorine-containing nitroazole derivatives, benzamide, nicotinamide, acridine-intercalator, 5-thiotretrazole derivative, 3-nitro-1,2,4-triazole, 4,5-dinitroimidazole derivative, hydroxylated texaphrins, cisplatin, mitomycin, tiripazamine, nitrosourea, mercaptopurine, methotrexate, fluorouracil, bleomycin, vincristine, carboplatin, epirubicin, doxorubicin, cyclophosphamide, vindesine, etoposide, paclitaxel, heat (hyperthermia), and the like), radioprotectors (e.g., cysteamine, aminoalkyl dihydrogen phosphorothioates, amifostine (WR 2721), IL-1, IL-6, and the like). Radiosensitizers enhance the killing of tumor cells. Radioprotectors protect healthy tissue from the harmful effects of radiation.

Any type of radiation can be administered to an animal, so long as the dose of radiation is tolerated by the animal without unacceptable negative side-effects. Suitable types of radiotherapy include, for example, ionizing (electromagnetic) radiotherapy (e.g., X-rays or gamma rays) or particle beam radiation therapy (e.g., high linear energy radiation). Ionizing radiation is defined as radiation comprising particles or photons that have sufficient energy to produce ionization, i.e., gain or loss of electrons (as described in, for example, U.S. Pat. No. 5,770,581). The effects of radiation can be at least partially controlled by the clinician. In one embodiment, the dose of radiation is fractionated for maximal target cell exposure and reduced toxicity.

In one embodiment, the total dose of radiation administered to an animal is about 0.01 Gray (Gy) to about 100 Gy. In another embodiment, about 10 Gy to about 65 Gy (e.g., about 15 Gy, 20 Gy, 25 Gy, 30 Gy, 35 Gy, 40 Gy, 45 Gy, 50 Gy, 55 Gy, or 60 Gy) are administered over the course of treatment. While in some embodiments a complete dose of radiation can be administered over the course of one day, the total dose is ideally fractionated and administered over several days. Desirably, radiotherapy is administered over the course of at least about 3 days, e.g., at least 5, 7, 10, 14, 17, 21, 25, 28, 32, 35, 38, 42, 46, 52, or 56 days (about 1-8 weeks). Accordingly, a daily dose of radiation will comprise approximately 1-5 Gy (e.g., about 1 Gy, 1.5 Gy, 1.8 Gy, 2 Gy, 2.5 Gy, 2.8 Gy, 3 Gy, 3.2 Gy, 3.5 Gy, 3.8 Gy, 4 Gy, 4.2 Gy, or 4.5 Gy), or 1-2 Gy (e.g., 1.5-2 Gy). The daily dose of radiation should be sufficient to induce destruction of the targeted cells. If stretched over a period, in one embodiment, radiation is not administered every day, thereby allowing the animal to rest and the effects of the therapy to be realized. For example, radiation desirably is administered on 5 consecutive days, and not administered on 2 days, for each week of treatment, thereby allowing 2 days of rest per week. However, radiation can be administered 1 day/week, 2 days/week, 3 days/week, 4 days/week, 5 days/week, 6 days/week, or all 7 days/week, depending on the animal's responsiveness and any potential side effects. Radiation therapy can be initiated at any time in the therapeutic period. In one embodiment, radiation is initiated in week 1 or week 2, and is administered for the remaining duration of the therapeutic period. For example, radiation is administered in weeks 1-6 or in weeks 2-6 of a therapeutic period comprising 6 weeks for treating, for instance, a solid tumor. Alternatively, radiation is administered in weeks 1-5 or weeks 2-5 of a therapeutic period comprising 5 weeks. These exemplary radiotherapy administration schedules are not intended, however, to limit the present invention.

In some embodiments of the present invention, a compound of the invention and one or more therapeutic agents or anticancer agents are administered to an animal under one or more of the following conditions: at different periodicities, at different durations, at different concentrations, by different administration routes, etc. In some embodiments, the compound is administered prior to the therapeutic or anticancer agent (e.g., radiation therapy), e.g., 0.5, 1, 2, 3, 4, 5, 10, 12, or 18 hours, 1, 2, 3, 4, 5, or 6 days, or 1, 2, 3, or 4 weeks prior to the administration of the therapeutic or anticancer agent. In some embodiments, the compound is administered after the therapeutic or anticancer agent, e.g., 0.5, 1, 2, 3, 4, 5, 10, 12, or 18 hours, 1, 2, 3, 4, 5, or 6 days, or 1, 2, 3, or 4 weeks after the administration of the anticancer agent. In some embodiments, the compound and the therapeutic or anticancer agent are administered concurrently but on different schedules, e.g., the compound is administered daily while the therapeutic or anticancer agent is administered once a week, once every two weeks, once every three weeks, or once every four weeks. In other embodiments, the compound is administered once a week while the therapeutic or anticancer agent is administered daily, once a week, once every two weeks, once every three weeks, or once every four weeks.

Compositions within the scope of this invention include all compositions wherein the compounds of the present invention are contained in an amount which is effective to achieve its intended purpose. While individual needs vary, determination of optimal ranges of effective amounts of each component is within the skill of the art. Typically, the compounds may be administered to mammals, e.g. humans, orally at a dose of 0.0025 to 50 mg/kg, or an equivalent amount of the pharmaceutically acceptable salt thereof, per day of the body weight of the mammal being treated for disorders responsive to induction of apoptosis. In one embodiment, about 0.01 to about 25 mg/kg is orally administered to treat, ameliorate, or prevent such disorders. For intramuscular injection, the dose is generally about one-half of the oral dose. For example, a suitable intramuscular dose would be about 0.0025 to about 25 mg/kg, or from about 0.01 to about 5 mg/kg.

The unit oral dose may comprise from about 0.01 to about 1000 mg, for example, about 0.1 to about 100 mg of the compound. The unit dose may be administered one or more times daily as one or more tablets or capsules each containing from about 0.1 to about 10 mg, conveniently about 0.25 to 50 mg of the compound or its solvates.

In a topical formulation, the compound may be present at a concentration of about 0.01 to 100 mg per gram of carrier. In a one embodiment, the compound is present at a concentration of about 0.07-1.0 mg/ml, for example, about 0.1-0.5 mg/ml, and in one embodiment, about 0.4 mg/ml.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. The preparations, particularly those preparations which can be administered orally or topically and which can be used for one type of administration, such as tablets, dragees, slow release lozenges and capsules, mouth rinses and mouth washes, gels, liquid suspensions, hair rinses, hair gels, shampoos and also preparations which can be administered rectally, such as suppositories, as well as suitable solutions for administration by intravenous infusion, injection, topically or orally, contain from about 0.01 to 99 percent, in one embodiment from about 0.25 to 75 percent of active compound(s), together with the excipient.

The pharmaceutical compositions of the invention may be administered to any patient who may experience the beneficial effects of the compounds of the invention. Foremost among such patients are mammals, e.g., humans, although the invention is not intended to be so limited. Other patients include veterinary animals (cows, sheep, pigs, horses, dogs, cats and the like).

The compounds and pharmaceutical compositions thereof may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are in one embodiment dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400. Aqueous injection suspensions may contain substances which increase the viscosity of the suspension which include, for example, sodium carboxymethyl cellulose, sorbitol, and/or dextran. Optionally, the suspension may also contain stabilizers.

The topical compositions of this invention are formulated in one embodiment as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The carriers may be those in which the active ingredient is soluble. Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762.

Ointments may be formulated by mixing a solution of the active ingredient in a vegetable oil such as almond oil with warm soft paraffin and allowing the mixture to cool. A typical example of such an ointment is one which includes about 30% almond oil and about 70% white soft paraffin by weight. Lotions may be conveniently prepared by dissolving the active ingredient, in a suitable high molecular weight alcohol such as propylene glycol or polyethylene glycol.

One of ordinary skill in the art will readily recognize that the foregoing represents merely a detailed description of certain preferred embodiments of the present invention. Various modifications and alterations of the compositions and methods described above can readily be achieved using expertise available in the art and are within the scope of the invention.

EXAMPLES

The following examples are illustrative, but not limiting, of the compounds, compositions, and methods of the present invention. Other suitable modifications and adaptations of the variety of conditions and parameters normally encountered in clinical therapy and which are obvious to those skilled in the art are within the spirit and scope of the invention.

Example I

This example describes in silico high-throughput and biological screening of potential inhibitors of the Ku70/80-DNA interaction.

Experiments were conducted for purposes of identifying a prospective binding pocket in the Ku70/80 heterodimer with proximity to the DNA-interaction region. In order to accomplish this, the published crystal structures of the Ku70/80 heterodimer (PDB ID 1JEQ) and the Ku70/80 dimer bound to a 55-nucleotide DNA substrate (PDB ID 1JEY) were utilized (see, e.g., Walker, et al., Nature, 412 (2001), pp. 607-614). A visually identified putative binding pocket based on four Ku70 residues (TYR400, LEU256, PHE436, and TYR409) and three Ku80 residues (GLN269, ASN359 and ARG486) was chosen and a representation of an idealized ligand ('protomol') was generated utilizing Surflex-Dock software. The prospective binding pocket is located at an ideal location in close proximity to the central canal which holds the DNA helix (FIG. 2A). It also spans the interface between the Ku70 and Ku80 subunits (FIG. 2A). Therefore, binding of a small molecule in this pocket could potentially disrupt the Ku70/80-DNA interaction, as well as interfere with Ku70-Ku80 interaction within the heterodimer itself. Interestingly, the automated Surflex-Dock 'pocket' finder only partially selected the visually identified pocket.

Next, the described 'protomol' was utilized as a guide to screen small molecule databases for potential inhibitors. Hits were sorted from highest to lowest docking scores and nine compounds were ultimately chosen for biological activity screening (see, Table 1). These compounds were commercially obtained and designated with a letter (A through H, and L). For initial activity screening experiments utilized an Electrophoretic Mobility Shift Assay (EMSA), in which a radioactively labeled artificial DNA substrate was incubated with a preparation of purified Ku70/80 protein, followed by non-denaturing gel electrophoresis. Interaction of Ku70/80 with DNA caused a measurable shift of the DNA band. Candidate compounds were then added to the EMSA reaction mixture at an initial concentration of 100 µM and disruption of the Ku70/80-DNA interaction (as defined by disappearance of the band shift) was observed for Compounds C and L (FIG. 3A). The other compounds did not display Ku-inhibitory activity at the relatively high concentration of 100 µM and were therefore discarded as potential candidates. Compounds C and L were further investigated for their ability to disrupt the Ku70/80 DNA interaction as well as Ku-dependent activation of the DNA-PKcs kinase.

TABLE 1

List of names and structures of the candidate compounds selected for activity screening in the EMSA assay. Names follow the ZINC database format (Irwin et al., 2012) and structures are derived from the online SEA search tool (SEArch).

| | Compound name | Identifier | Structure |
|---|---|---|---|
| A | 2-amino-6-[4-[(7-methoxy-1,3-benzodioxol-5-yl)methyl]piperazin-1-yl]pyrimidin-4-ol | ZINC 65397319 | 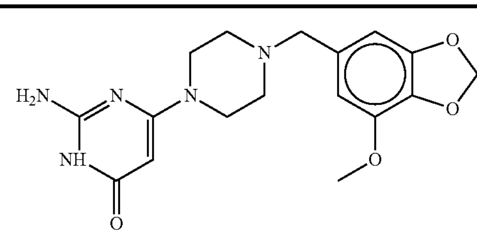 |

TABLE 1-continued

List of names and structures of the candidate compounds selected for activity screening in the EMSA assay. Names follow the ZINC database format (Irwin et al., 2012) and structures are derived from the online SEA search tool (SEArch).

| | Compound name | Identifier | Structure |
|---|---|---|---|
| B | N'-(4-ethylphenyl)-6-[[4-(4-methoxyphenyl)piperazin-1-yl]methyl]-1,3,5-triazine-2,4-diamine | ZINC 05274618 | 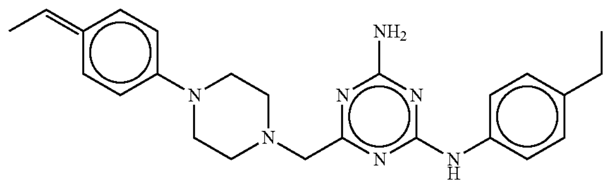 |
| C | 4-[[4-(4-methoxyphenyl)piperazin-1-yl]methyl]-6-(m-tolyimino)-5H-1,3,5-triazin-2-amine | ZINC 09009828 | 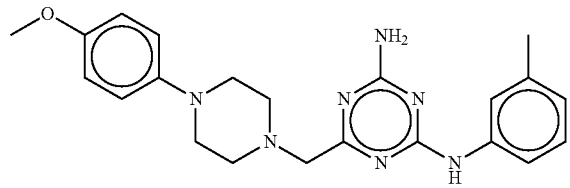 |
| D | 2-amino-7-[3-(4-methoxyphenyl)propanoyl]-3,5,6,8-tetrahydroprido[3,4-d]pyrimidin-4-one | ZINC 71760384 | 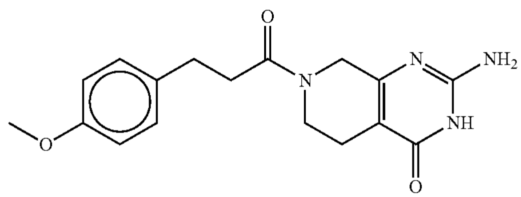 |
| E | 2-amino-7-[(2R)-2-(dimethylamino)-2-(p-tolyl)acetyl]-3,5,6,8-tetrahydropyrido[3,4-d]pyrimidin-4-one | ZINC 72129532 | 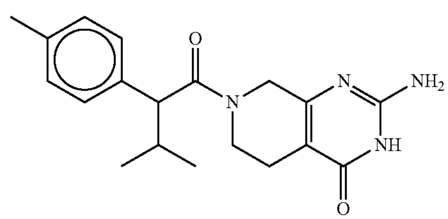 |
| F | 2-amino-4-[2-oxo-2-[4-(4-phenyl-1H-pyrazol-5-yl)-1-piperidyl]ethyl]-1H-pyrimidin-6-one | ZINC 67934662 | 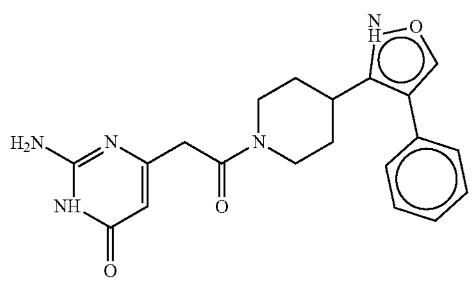 |
| G | 2-(2-amino-6-oxo-1,6-dihydropyrimidin-5-yl)-N-butyl-N-(2-fluorobenzyl)acetamide | Chembridge 31076279 | 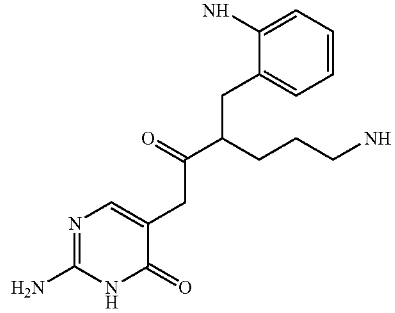 [SMILES: NCCCC(Cc1ccccc1N)C(=O)Cc1cnc(N)[nH]c1=O] |

TABLE 1-continued

List of names and structures of the candidate compounds selected for activity screening in the EMSA assay. Names follow the ZINC database format (Irwin et al., 2012) and structures are derived from the online SEA search tool (SEArch).

| | Compound name | Identifier | Structure |
|---|---|---|---|
| H | 2-amino-6-[4-[(1-propylimidazol-2-yl)methyl]piperazin-1-yl]pyrimidin-4-ol | ZINC 65492442 | 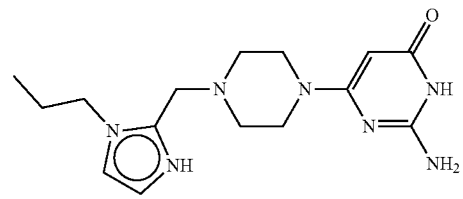 |
| L | 7-[[2-(3,4-dimethoxyphenyl)ethyl]amino]-3-(3-fluorophenyl)pyrimido[4,5-d]pyrimidine-2,4(1H,3H)-dione | Vitas-M STL127705 | 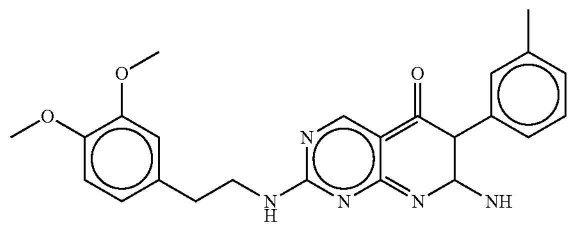 |

Example II

This example demonstrates that Compound L inhibits binding of Ku70/80 to DNA, as well as Ku-dependent activation of the DNA-$PK_{CS}$ kinase.

After establishing the fact that both Compounds C and L displayed an ability to disrupt Ku-DNA binding, a dose-response curve was next obtained. Therefore, a two orders of magnitude range of serial dilutions of the compounds was added to the previously described EMSA reactions. Inhibition of Ku-DNA interaction in a straight forward dose-dependent manner by compound L alone was observed (FIG. 3B). In order to quantify the relative efficiency of Ku-DNA binding for each dose of Compound L, the intensity of the Ku-DNA bands in the EMSA assay was measured and normalized those values to a number between 0 and 100, where the value 0 represents a reaction where no Ku70/80 was present and the value 100 represents a reaction where no inhibitor was added. These normalized values were subsequently plotted against the corresponding concentrations of Compound L (FIG. 3B). A logarithmic trend line was added and equations were obtained to describe the dose-response curves of Compound L in the EMSA assay. This approach allowed calculation of the dose needed to inhibit 50% of maximal Ku-DNA binding ($IC_{50}$) at 3.5 μM. These experiments demonstrate that Compounds L effectively disrupts association of the Ku70/80 heterodimer with a DNA substrate in vitro at $IC_{50}$ values in the lower micro-molar range. $IC_{50}$ values in this range are generally considered to be a viable starting point for lead-finding exploits.

Figure 4:
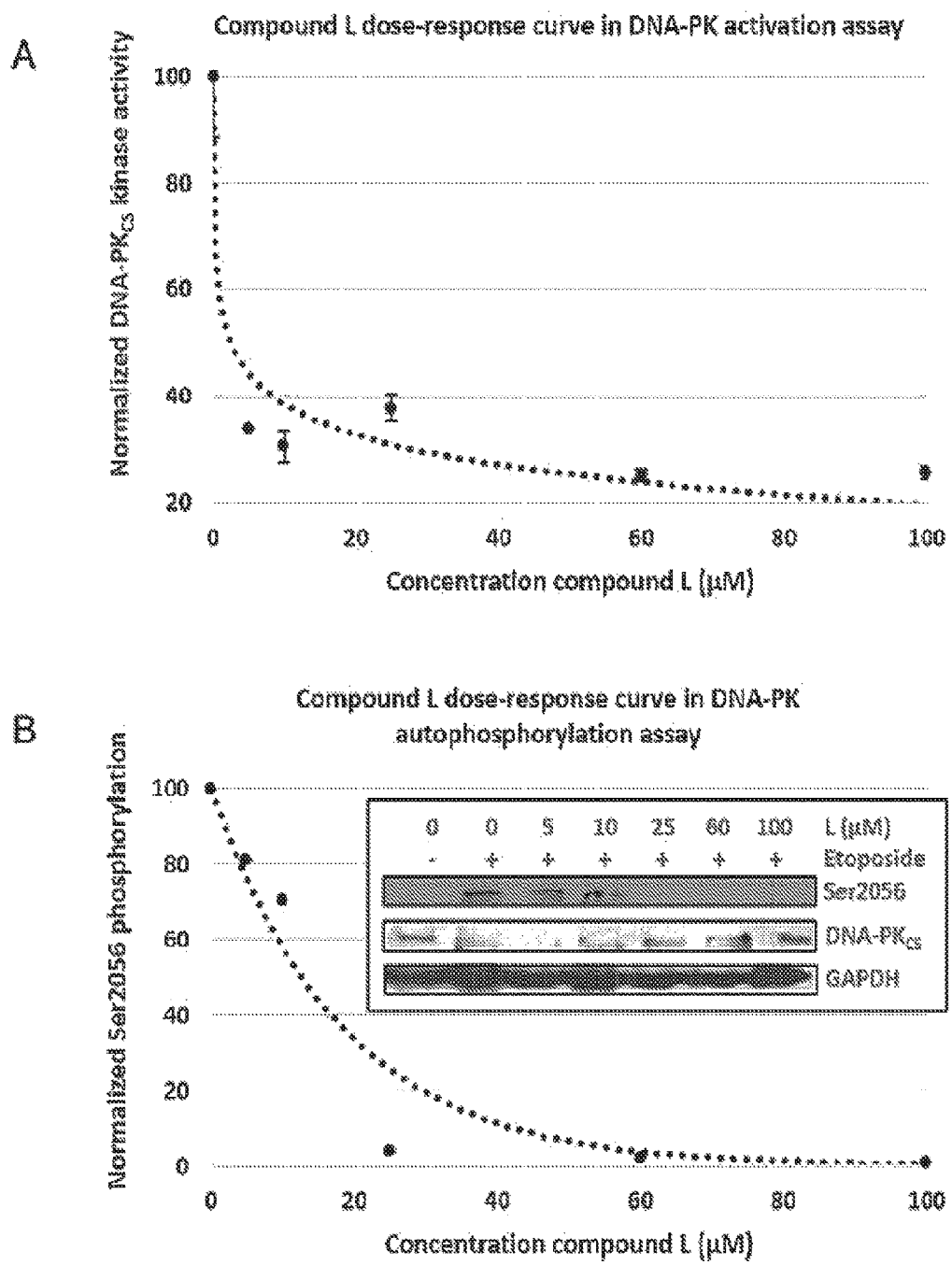
FIG. 4A-B. Compound L inhibits Ku-dependent activation of the DNA-$PK_{CS}$ kinase in vitro and in vivo. (A) Titration of Compound L in the DNA-$PK_{CS}$ kinase activity assay, measuring in vitro phosphorylation of a p53-based peptide substrate. A logarithmic trend line (dotted line) is added. An $IC_{50}$ of 2.5 µM can be calculated from this graph. Error bars represent standard deviations. (B) Titration of Compound L in the DNA-$PK_{CS}$ autophosphorylation assay, measuring in vivo autophosphorylation of the DNA-$PK_{CS}$ SER2056 residue. Inlay: top panel=DNA-$PK_{CS}$ SER2056, middle panel=total DNA-$PK_{CS}$, bottom panel=loading control GAPDH.

To further validate the Ku-inhibitory activity of Compound L, experiments examined its effects on Ku-dependent activation of the DNA-$PK_{CS}$ kinase. The Ku70/80 heterodimer does not display a clear enzymatic activity of its own which can be quantified. It is, however, a potent co-factor for the activation of other NHEJ enzymes, including DNA-$PK_{CS}$ (see, G. C. Smith, et al., Genes Dev., 13 (1999), pp. 916-934). It was therefore reasoned that disruption of the Ku-DNA interaction by Compound L should also diminish DNA-$PK_{CS}$ kinase activity. The DNA-$PK_{CS}$ kinase has multiple known downstream targets, including p53, Artemis, and DNA-$PK_{CS}$ itself (see, E. Weterings, et al., Cell Res., 18 (2008), pp. 114-124; G. C. Smith, et al., Genes Dev., 13 (1999), pp. 916-934). It is at present not entirely clear which targets are critical for the overall DNA repair response, but it is evident that the kinase domain of DNA-$PK_{CS}$ is indispensable. Experiments therefore quantified the kinase activity of a purified preparation of the DNA-$PK_{CS}$ protein in the presence of different concentrations of Compound L. Experiments measured the phosphorylation of a p53-based peptide substrate as an arbitrary reporter of DNA-$PK_{CS}$ kinase activity. The obtained in vitro DNA-$PK_{CS}$ kinase activities were subsequently normalized and plotted as a function of compound L concentration (FIG. 4A). Experiments observed a sharp dose-dependent inhibition of DNA-$PK_{CS}$ kinase activity. The obtained dose-response curve was fitted with a logarithmic trend line and an $IC_{50}$ value of 2.5 μM was calculated. Therefore, both primary (EMSA) and secondary (DNA-$PK_{CS}$ activity) assays for the Ku-inhibitory potential of Compound L indicate an $IC_{50}$ value in the lower micro-molar range.

In order to further examine the effects of Compound L on Ku-dependent activation of the DNA-$PK_{CS}$ kinase in vivo, experiments also exposed cultures of the human glioblastoma cell line SF-767 to increasing concentrations of Compound L. Upon induction of DSBs by etoposide, experiments quantified the levels of DNA-$PK_{CS}$ autophosphorylation at the SER2056 residue by means of Western blot analysis (FIG. 4B). Experiments observed a sharp decline in DNA-$PK_{CS}$ autophosphorylation with increasing doses of Compound L. As expected, total DNA-$PK_{CS}$ was not suppressed by Compound L. This data effectively proves that Compound L is capable of inhibiting the Ku-dependent activation of the DNA-$PK_{CS}$ kinase in human cells.

Example III

This example demonstrates that Compound L is predicted to form hydrogen bonds with at least four amino acid residues in the putative binding pocket of Ku70/80.

After having established that Compound L displays a distinct Ku-inhibitory activity, experiments proceeded to investigate the predicted fit of this compound into the Ku70/80 putative binding pocket (FIG. 2A). Virtual docking of the structure of Compound L with the aid of Surflex-Dock software, revealed that this compound occupies most of the available space in the putative pocket and is predicted to form hydrogen bonds with the SER257 and ARG363 amino acid residues of Ku70 and the GLN269 and ARG486 residues of Ku80 (FIG. 2B). Both the Ku70 and Ku80 subunits are predicted to contribute to the interaction surface between Compound L and the prospective pocket, with Ku70 being the predominant contributor (FIG. 2C).

Example IV

This example demonstrates that Compound L sensitizes human cell lines to ionizing radiation.

Figure 5:
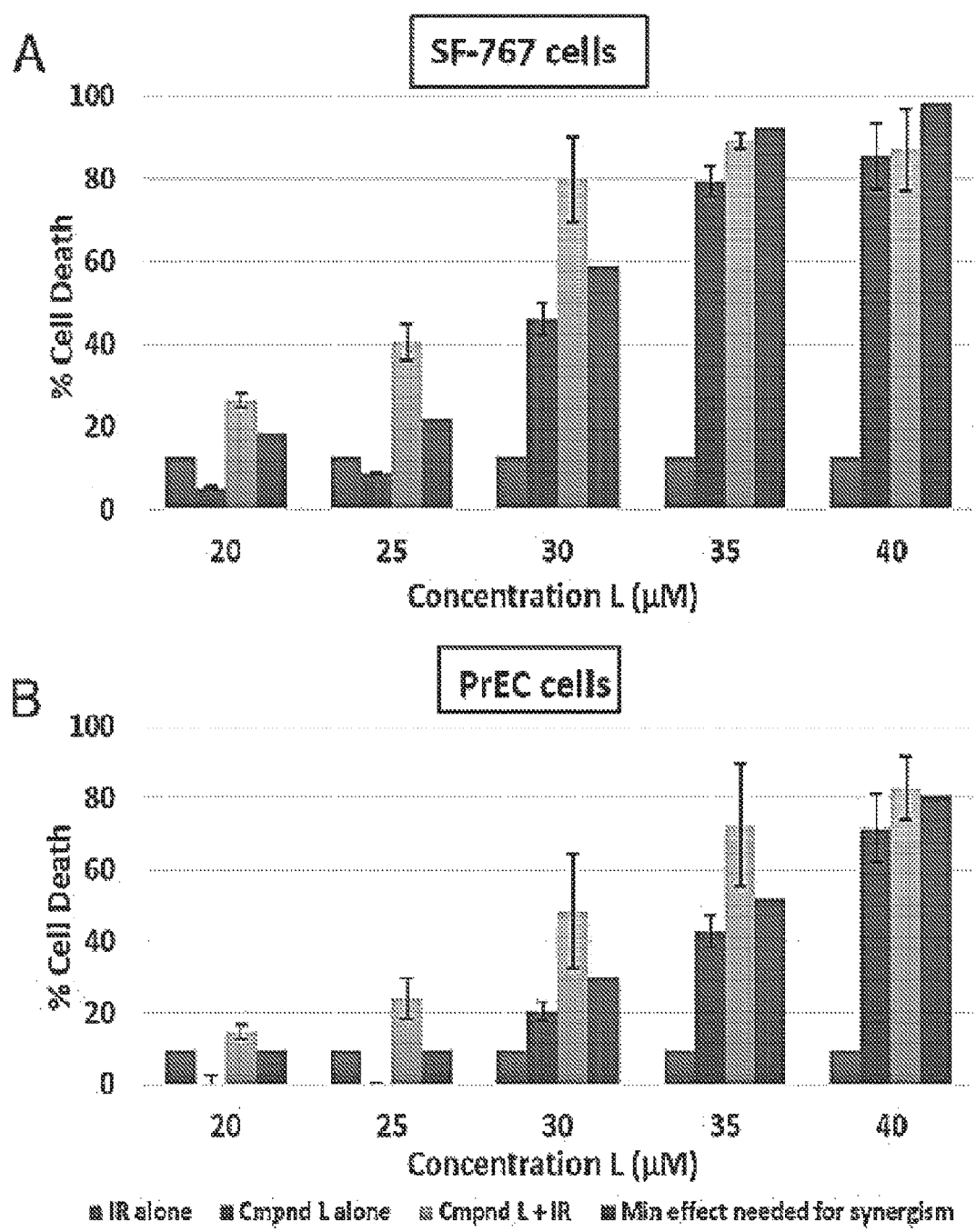
FIG. 5A-B. Compound L synergistically sensitizes human cell lines to radiation at sub-cytotoxic concentrations. (A) SF-767 glioblastoma cells, (B) hTERT immortalized prostate epithelial (PrEC) cells. Relative percentage of cell death as a results of increasing doses of Compound L as a single modality (red columns—second column from left), radiation as a single modality (blue column—first column from left), and a combination of Compound L and radiation (green columns—third column from left). Purple columns represent the sum of the effects of single treatment modalities. Synergistic radiation-sensitization exists where the effects of the combination treatment (green columns—third column from left) exceeds the effects of the sum of the single modality treatments (purple columns—fourth column from left). Error bars represent standard deviations.

Data demonstrated that Compound L possesses a potential to disrupt the NHEJ process by interfering with the binding of Ku70/80 to DNA and by inhibiting the subsequent activation of the DNA-$PK_{CS}$ kinase. Consequently, this substance could have an effect on the efficiency of overall repair of DSBs. In order to examine this potential, experiments tested Compound L for its ability to potentiate the effects of ionizing radiation on two human cell lines: the glioblastoma cell line SF-767 (FIG. 5A), and an hTERT immortalized prostate epithelial (PrEC) cell line (see, R. Berger, et al., Cancer Res., 64 (2004), pp. 8867-8875) (FIG. 5B). Cultured cells were treated with either the compound as a single modality, ionizing radiation as a single modality or with a regimen of concurrent radiation and compound. Cell viability was measured after a six day recovery period by standard MTS assay and normalized to the untreated control (no compound or radiation). FIG. 5 presents the observed effects of each treatment modality in terms of percentage non-viable cells. The effects are plotted as a function of the compound's concentration in the culture medium.

As expected, experiments observed a clear, dose-dependent increase in non-viable cell population with increasing concentrations of Compound L (FIG. 5, red columns). This reflects the fundamental cytotoxicity of the compound under the chosen experimental conditions. In both cell lines, toxicity of Compound L stayed low (below 5% non-viability) up to 25 µM, after which an exponential increase in cytotoxicity was observed. Interestingly, at low cytotoxic concentrations the effects of a combined treatment consisting of concurrent compound L and radiation far exceeded the effects observed with either compound or radiation as a single modality (FIG. 5, green columns). In order to exclude the possibility that this phenomenon was caused by mere additive effects, experiments calculated the sum of the effects of the single modalities (FIG. 5, purple columns) and compared the obtained values with the effects of the combination treatments. By definition, synergism is present when the effect of the combination therapy (green columns) exceeds the sum of the effects of the single modalities (purple columns). In SF-767 cells, synergism was most clearly observed between 20 and 30 µM (FIG. 5A) and in immortalized PrEC cells synergism was present in the 20-35 µM range (FIG. 5B).

These effects demonstrate that Compound L synergistically sensitizes at least two human cell lines to radiation treatment. The therapeutic range of Compound L, however, is close to the dose where cytotoxicity starts increasing rapidly and further medicinal chemistry is likely necessary in order to reduce toxicity of this compound or its derivatives. Nevertheless, this novel inhibitor has shown clear evidence for DNA repair modulating activity and consequently holds great potential for future development into a lead compound.

Example V

This example demonstrates that Compound L is capable of suppressing the repair of radiation-induced DNA double strand breaks (DSBs) in living cells. This repair process is dependent on active Ku70/80 and the suppression of Ku-dependent DSB repair is further proof that Compound L inhibits Ku70/80 activity. The relative amount of DSBs is measured by counting the relative intensity of a canonical DSB marker: γ-H2AX.

Figure 6:
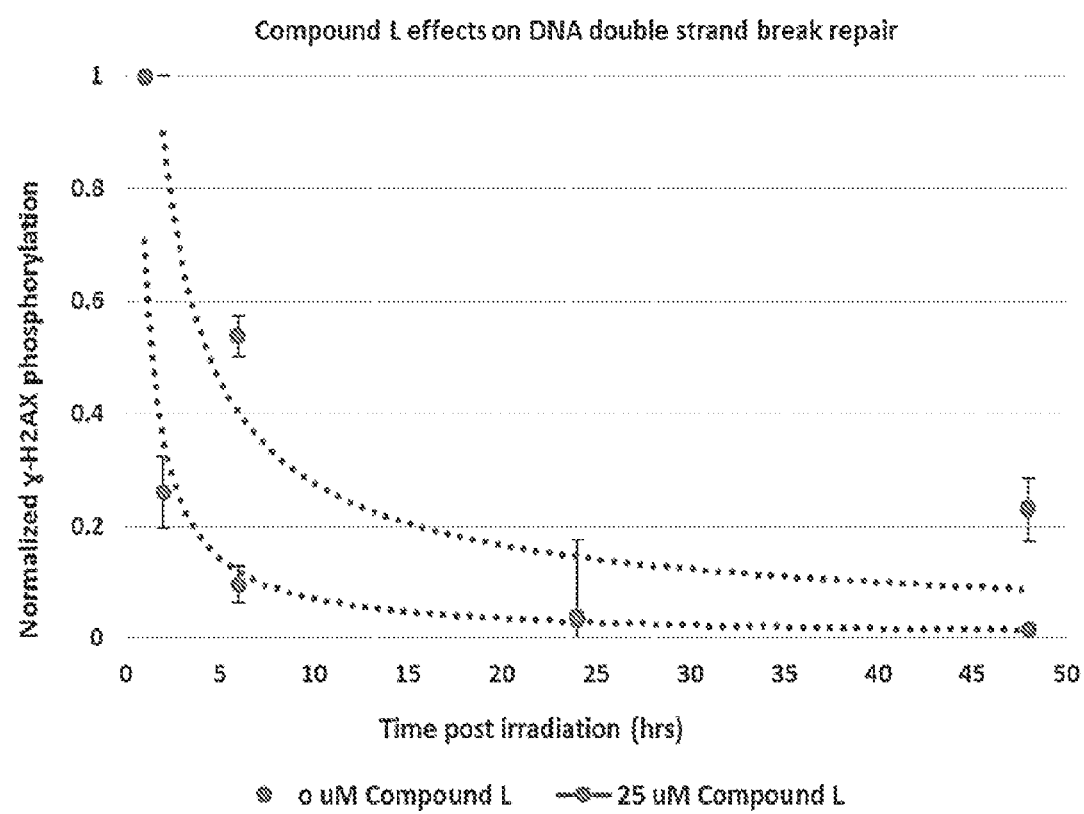
FIG. 6. Compound L impairs DNA double strand break (DSB) repair. Relative number of DSBs was measured by quantifying and normalizing γ-H2AX phosphorylation. Relative amount of DSBs was shown to rise initially post radiation, but diminished fast in the untreated control as a result of active DSB repair. Repair kinetics in cells treated with 25 µM Compound L was significantly delayed. Measured in human glioblastoma cells (SF767). Error bars represent standard error.

FIG. 6 shows that Compound L impairs DNA double strand break (DSB) repair. Relative number of DSBs was measured by quantifying and normalizing γ-H2AX phosphorylation. Relative amount of DSBs was shown to rise initially post radiation, but diminished fast in the untreated control as a result of active DSB repair. Repair kinetics in cells treated with 25 µM Compound L was significantly delayed. Measured in human glioblastoma cells (SF767). Error bars represent standard error.

Example VI

This example demonstrates the pharmacokinetic profile of Compound L in nude mice. Based on this profile, a half-life of approximately 1.5 hrs can be estimated, which is favorable for the purpose of radiation sensitization of human tumors, where dosing with compound is shortly followed by radiation therapy. A single bolus IP injection of 5 mg/kg of Compound L was well tolerated and did not reveal any acute toxicity. After two weeks, histopathology and comprehensive blood panels showed no abnormalities. These findings demonstrate that Compound L is well tolerated in mice and that further efficacy testing in mouse models will likely not be compromised by toxicity issues.

Figure 7:
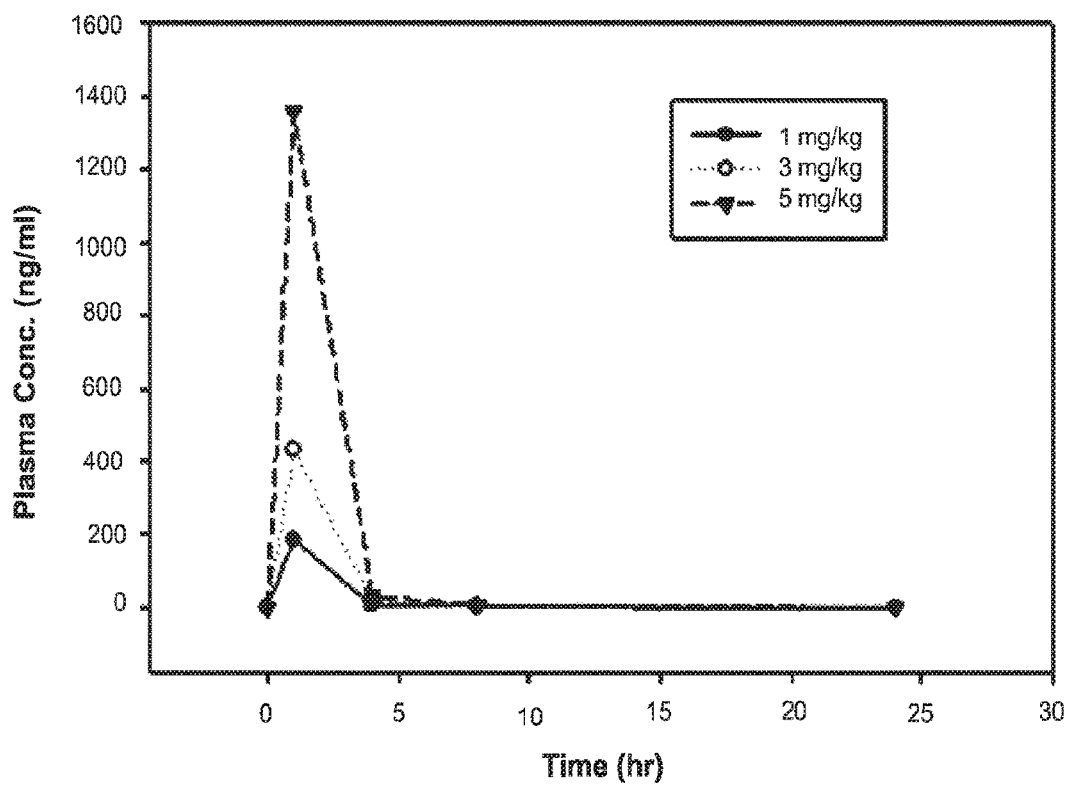
FIG. 7 shows that Compound L is well tolerated in a mouse model and has a short plasma half-life. A bolus IP injection of Compound L was given at either 1, 3, or 5 mg/kg and plasma levels of Compound L were determined by LC-MS. Plasma levels are directly proportional to dose. Plasma half-life can be estimated at 1.5 hours. A two week follow-up did not reveal signs of toxicity and histopathology and comprehensive blood panels were found to be normal.

FIG. 7 shows that Compound L is well tolerated in a mouse model and has a short plasma half-life. A bolus IP injection of Compound L was given at either 1, 3, or 5 mg/kg and plasma levels of Compound L were determined by LC-MS. Plasma levels are directly proportional to dose. Plasma half-life can be estimated at 1.5 hours. A two week follow-up did not reveal signs of toxicity and histopathology and comprehensive blood panels were found to be normal.

Example VII

This example compares the in vitro activity of several structural analogs of Compound L. This assay measures the effect of each compound on the in vitro activity of the DNA-$PK_{CS}$ kinase. The activity of this kinase is dependent on functional Ku70/80 and the dose-dependent suppression of DNA-$PK_{CS}$ kinase activity is proof that these compounds inhibit Ku70/80 activity in vitro.

Figure 8:
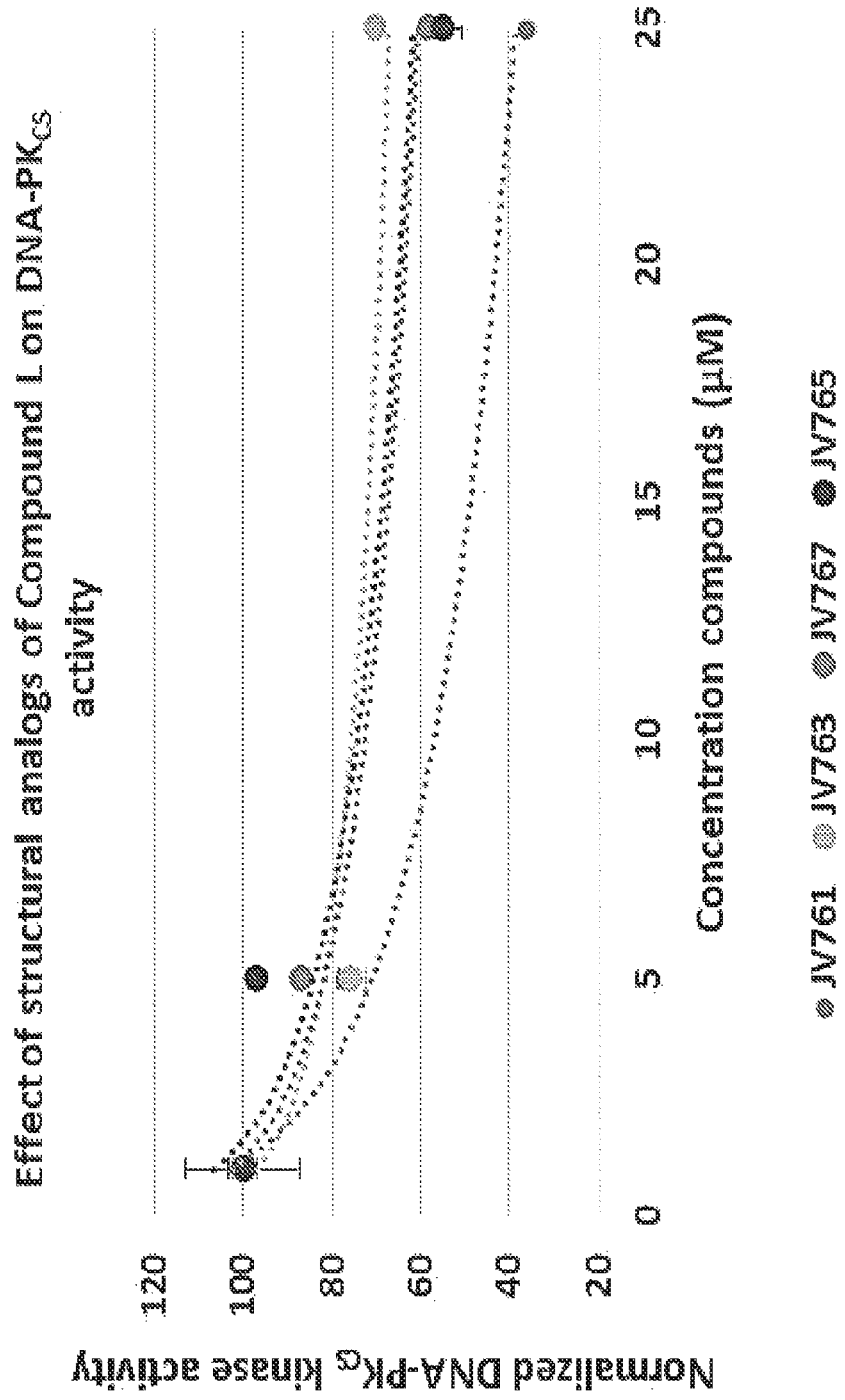
FIG. 8 demonstrates that structural analogs of Compound L impair Ku-dependent activation of the DNA-$PK_{CS}$ kinase in vitro. Titration of compounds JV761, JV763, JV767, and JV765 in the DNA-$PK_{CS}$ kinase assay, measuring Ku70/80-dependent in vitro phosphorylation of a p53-based peptide substrate. The compound JV761 was found to have a superior activity and an IC50 of 12 µM can be calculated from this graph.

FIG. 8 demonstrates that structural analogs of Compound L impair Ku-dependent activation of the DNA-$PK_{CS}$ kinase in vitro. Titration of compounds JV761, JV763, JV767, and JV765 in the DNA-$PK_{CS}$ kinase assay, measuring Ku70/80-dependent in vitro phosphorylation of a p53-based peptide substrate. The compound JV761 was found to have a superior activity and an IC50 of 12 µM can be calculated from this graph. As shown in FIG. 8 at the 25 µM location, JV761 has the lowest DNA-$PK_{CS}$ kinase inhibitory activity, followed by JV765, followed by JV767, and followed by JV763.

Example VIII

This example demonstrates the ability of Compound L and its structural analog JV761 to sensitize human cancer cells to radiation therapy. This is done by means of a standard MTS assay, measuring survival of human glioblastoma (SF767) or immortalized prostate epithelial (PrEC) cells 7 days after treatment with compounds and radiation therapy. It demonstrates that JV761 synergistically sensitizes cancer cells to radiation at a significantly lower concentration than Compound L does (1-5 µM vs 20-30 µM). The radiation-sensitizing potential of Compound L and JV761 is attributable to the ability of these compounds to suppress the activity of Ku70/80 in vivo.

Figure 9:
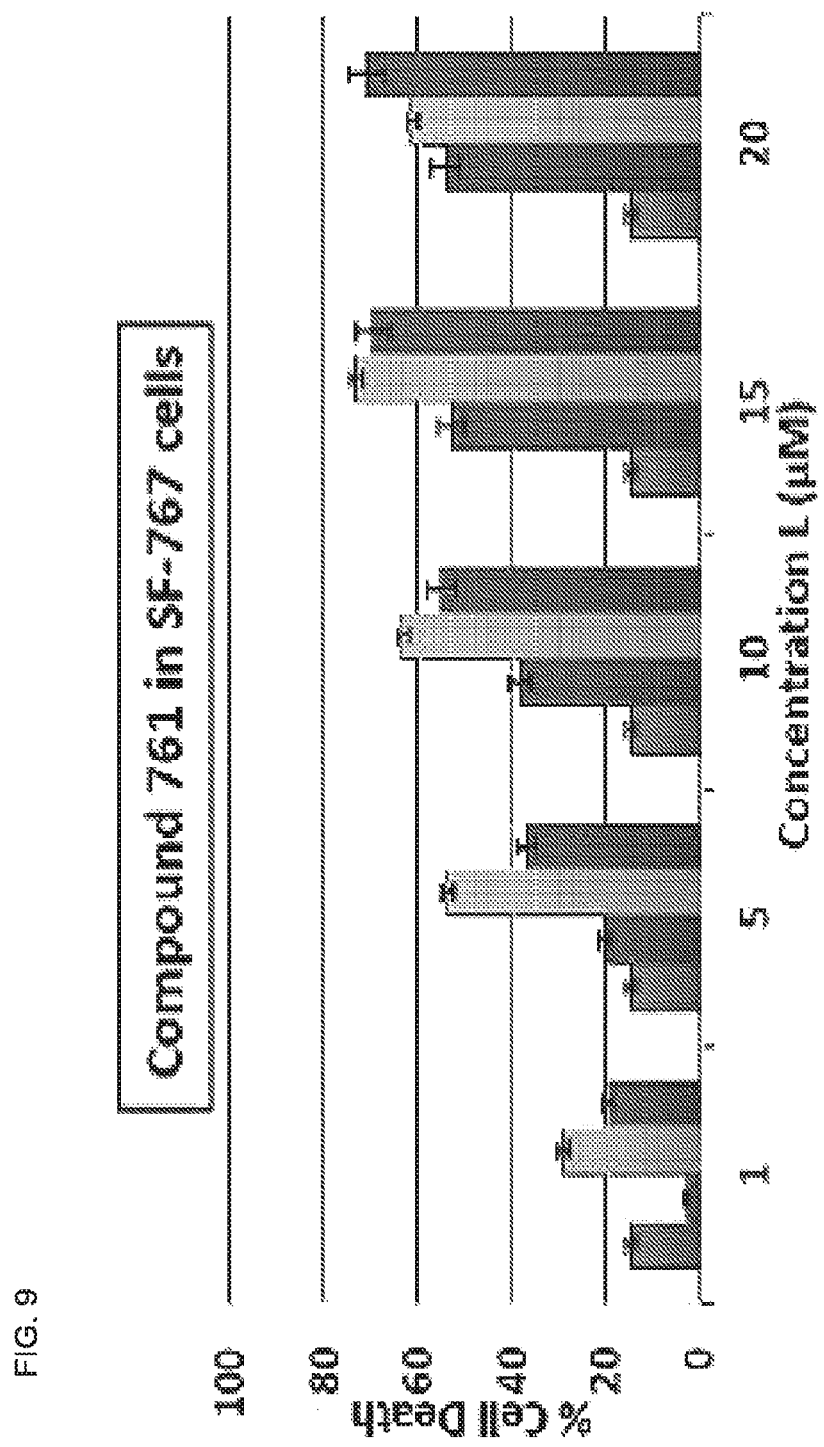
FIG. 9 shows that Compound L and its structural analog JV761 synergistically sensitize human cancer cells to radiation therapy. Within FIG. 9, the order of the columns is from the farthest left, blue followed by red followed by green and followed by purple. Red columns: relative percentage of cell death as a result of increasing doses of Compound L (see, FIGS. 5A and 5B) or JV761 (FIG. 9) as a single modality. Blue columns: cell death as a result of 4Gy radiation therapy as a single modality. Green columns: cell death as a result of a combination of Compound L or JV761 and radiation therapy. Purple columns: sum of the effects of single treatment modalities. Synergistic radiation-sensitization exists where the effects of the combination treatment (green columns) exceeds the effects of the sum of the single modality treatments (purple columns). Error bars represent standard deviations. Synergism can be detected between 20-30 µM for Compound L and between 1-5 µM for JV761.

FIG. 9 shows that Compound L and its structural analog JV761 synergistically sensitize human cancer cells to radiation therapy. Within FIG. 9, the order of the columns is from the farthest left, blue followed by red followed by green and followed by purple. Red columns: relative percentage of cell death as a result of increasing doses of Compound L (see, FIGS. 5A and 5B) or JV761 (FIG. 9) as a single modality. Blue columns: cell death as a result of 4Gy radiation therapy as a single modality. Green columns: cell death as a result of a combination of Compound L or JV761 and radiation therapy. Purple columns: sum of the effects of single treatment modalities. Synergistic radiation-sensitization exists where the effects of the combination treatment (green columns) exceeds the effects of the sum of the single modality treatments (purple columns). Error bars represent standard deviations. Synergism can be detected between 20-30 µM for Compound L and between 1-5 µM for JV761.

Having now fully described the invention, it will be understood by those of skill in the art that the same can be performed within a wide and equivalent range of conditions, formulations, and other parameters without affecting the scope of the invention or any embodiment thereof. All patents, patent applications and publications cited herein are fully incorporated by reference herein in their entirety.

INCORPORATION BY REFERENCE

The entire disclosure of each of the patent documents and scientific articles referred to herein is incorporated by reference for all purposes. The following references are referenced within this application and are herein incorporated by reference in all entireties:

An, J., M. Totrov, and R. Abagyan. 2004. Comprehensive identification of "druggable" protein ligand binding sites. Genome Inform. 15:31-41.

Bao, S., Q. Wu, R. E. McLendon, Y. Hao, Q. Shi, A. B. Hjelmeland, M. W. Dewhirst, D. D. Bigner, and J. N. Rich. 2006. Glioma stem cells promote radioresistance by preferential activation of the DNA damage response. Nature. 444:756-760.

Berger, P. G. Febbo, P. K. Majumder, J. J. Zhao, S. Mukherjee, S. Signoretti, K. T. Campbell, W. R. Sellers, T. M. Roberts, M. Loda, T. R. Golub, W. C. Hahn; Androgen-induced differentiation and tumorigenicity of human prostate epithelial cells; Cancer Res., 64 (2004), pp. 8867-8875.

Beskow, C., J. Skikuniene, A. Holgersson, B. Nilsson, R. Lewensohn, L. Kanter, and K. Viktorsson. 2009. Radioresistant cervical cancer shows upregulation of the NHEJ proteins DNA-PK$_{CS}$, Ku70 and Ku86. Br J Cancer. 101: 816-821.

Curtin, N. J. 2012. DNA repair dysregulation from cancer driver to therapeutic target. Nat Rev Cancer. 12:801-817.

Eisenbrey, L. Albala, M. R. Kramer, N. Daroshefski, D. Brown, J. B. Liu, M. Stanczak, P. O'Kane, F. Forsberg, M. A. Wheatley; Development of an ultrasound sensitive oxygen carrier for oxygen delivery to hypoxic tissue; Int. J. Pharm., 478 (2015), pp. 361-367.

Fattah, B. L. Ruis, E. A. Hendrickson; Mutations to Ku reveal differences in human somatic cell lines; DNA Repair (Amst.), 7 (2008), pp. 762-774.

Ghezraoui, H., M. Piganeau, B. Renouf, J. B. Renaud, A. Sallmyr, B. Ruis, S. Oh, A. E. Tomkinson, E. A. Hendrickson, C. Giovannangeli, M. Jasin, and E. Brunet. 2014. Chromosomal translocations in human cells are generated by canonical nonhomologous end-joining. Mol Cell. 55:829-842.

Gu, Y., S. Jin, Y. Gao, D. T. Weaver, and F. W. Alt. 1997. Ku70-deficient embryonic stem cells have increased ionizing radiosensitivity, defective DNA end-binding activity, and inability to support V(D)J recombination. Proc Natl Acad Sci USA. 94:8076-8081.

Han, S., J. C. Brenner, A. Sabolch, W. Jackson, C. Speers, K. Wilder-Romans, K. E. Knudsen, T. S. Lawrence, A. M. Chinnaiyan, and F. Y. Feng. 2013. Targeted radiosensitization of ETS fusion-positive prostate cancer through PARP1 inhibition. Neoplasia. 15:1207-1217.

Irwin, J. J., T. Sterling, M. M. Mysinger, E. S. Bolstad, and R. G. Coleman. 2012. ZINC: a free tool to discover chemistry for biology. J Chem Inf Model. 52:1757-1768.

Jaamaa, S., and M. Laiho. 2012. Maintenance of genomic integrity after DNA double strand breaks in the human prostate and seminal vesicle epithelium: the best and the worst. Mol Oncol. 6:473-483.

Jekimovs, C., E. Bolderson, A. Suraweera, M. Adams, K. J. O'Byrne, and D. J. Richard. 2014. Chemotherapeutic compounds targeting the DNA double-strand break repair pathways: the good, the bad, and the promising. Front Oncol. 4:86.

Jubb, H., A. P. Higueruelo, A. Winter, and T. L. Blundell. 2012. Structural biology and drug discovery for protein-protein interactions. Trends Pharmacol Sci. 33:241-248.

Kim, S. H., D. Kim, J. S. Han, C. S. Jeong, B. S. Chung, C. D. Kang, and G. C. Li. 1999. Ku autoantigen affects the susceptibility to anticancer drugs. Cancer Res. 59:4012-4017.

Klibanov, T. I. Shevchenko, B. I. Raju, R. Seip, C. T. Chin; Ultrasound-triggered release of materials entrapped in microbubble-liposome constructs: a tool for targeted drug delivery; J. Control. Release, 148 (2010), pp. 13-17.

Kragelund, E. Weterings, R. Hartmann-Petersen, G. Keijzers; The Ku70/80 ring in Non-homologous End-joining: easy to slip on hard to remove; Front Biosci. (Landmark Ed), 21 (2016), pp. 514-527.

Li, Y. H., X. Wang, Y. Pan, D. H. Lee, D. Chowdhury, and A. C. Kimmelman. 2012. Inhibition of non-homologous end joining repair impairs pancreatic cancer growth and enhances radiation response. PLoS One. 7:e39588.

Moding, E. J., M. B. Kastan, and D. G. Kirsch. 2013. Strategies for optimizing the response of cancer and normal tissues to radiation. Nat Rev Drug Discov. 12:526-542.

Nimura, Y., T. Kawata, K. Uzawa, J. Okamura, C. Liu, M. Saito, H. Shimada, N. Seki, A. Nakagawara, H. Ito, T. Ochiai, and H. Tanzawa. 2007. Silencing Ku80 using small interfering RNA enhanced radiation sensitivity in vitro and in vivo. Int J Oncol. 30:1477-1484.

Perot, S., O. Sperandio, M. A. Miteva, A. C. Camproux, and B. O. Villoutreix. 2010. Druggable pockets and binding site centric chemical space: a paradigm shift in drug discovery. Drug Discov Today. 15:656-667.

Smith, G. C., and S. P. Jackson. 1999. The DNA-dependent protein kinase. Genes Dev. 13:916-934.

Walker, J. R., R. A. Corpina, and J. Goldberg. 2001. Structure of the Ku heterodimer bound to DNA and its implications for double-strand break repair. Nature. 412:607-614.

Welsh, J. W., D. Mahadevan, R. Ellsworth, L. Cooke, D. Bearss, and B. Stea. 2009. The c-Met receptor tyrosine kinase inhibitor MP470 radiosensitizes glioblastoma cells. Radiat Oncol. 4:69.

Weterings, E., and D. J. Chen. 2008. The endless tale of non-homologous end-joining. Cell Res. 18:114-124.

Weterings, E., N. S. Verkaik, H. T. Bruggenwirth, J. H. Hoeijmakers, and D. C. van Gent. 2003. The role of DNA dependent protein kinase in synapsis of DNA ends. Nucleic Acids Res. 31:7238-7246.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:
1. A compound selected from the group consisting of:

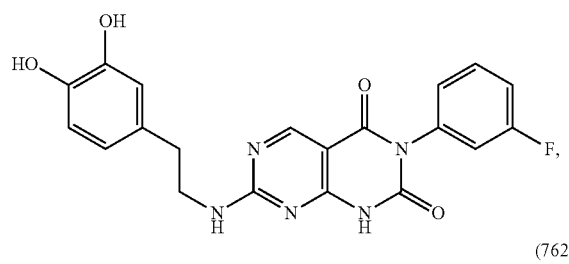

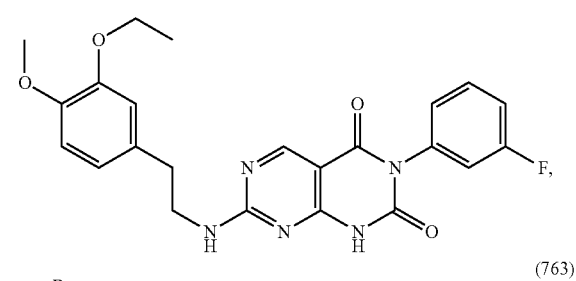

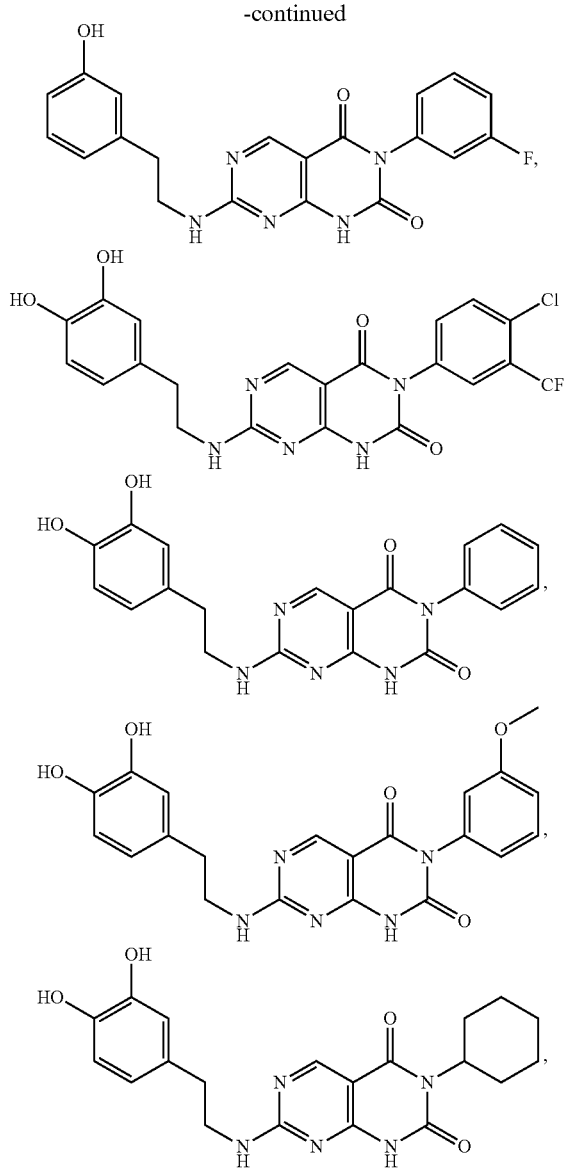

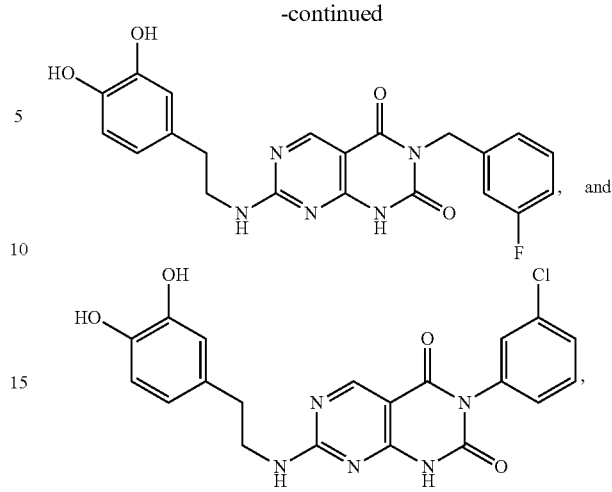

or a pharmaceutically acceptable salts, and/or solvates thereof.

2. A pharmaceutical composition comprising the compound of claim 1 and a pharmaceutically acceptable carrier.

3. A kit comprising a compound of claim 1 and instructions for administering said compound to a patient having a hyperproliferative disease, wherein said hyperproliferative disease is cancer.

4. The kit of claim 3, wherein the cancer is one or more selected from glioblastoma, prostate cancer, a solid cancer, and a hematologic cancer.

5. The kit of claim 3, wherein the cancer is characterized by aberrant Ku70/80 activity.

6. The kit of claim 3, wherein said cancer is any type of cancer having NHEJ pathway related activity.

7. The kit of claim 3, wherein the cancer is characterized by aberrant of DNA-PKcs activity.

8. The kit of claim 3, further comprising one or more anticancer agents.

9. The kit of claim 8, wherein said compound is to be administered together with one or more anticancer agents.

* * * * *